US012693686B2

(12) United States Patent
Dutta

(10) Patent No.: US 12,693,686 B2
(45) Date of Patent: Jul. 28, 2026

(54) DETERMINATION AND ALLEVIATION OF ROOT CAUSES FOR EMISSION OF POLLUTANTS FROM VEHICLES

(71) Applicant: International Business Machines Corporation, Armonk, NY (US)

(72) Inventor: Raja Dutta, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 120 days.

(21) Appl. No.: 18/914,795

(22) Filed: Oct. 14, 2024

(65) Prior Publication Data

US 2026/0104717 A1     Apr. 16, 2026

(51) Int. Cl.
| | |
|---|---|
| *G05D 1/69* | (2024.01) |
| *G01N 33/00* | (2006.01) |
| *G05D 101/15* | (2024.01) |
| *G05D 105/10* | (2024.01) |
| *G05D 107/00* | (2024.01) |
| *G05D 111/10* | (2024.01) |
(Continued)

(52) U.S. Cl.
CPC ........... *G05D 1/69* (2024.01); *G01N 33/0063* (2013.01); *G06F 40/20* (2020.01); *G06V 10/25* (2022.01); *G05D 2101/15* (2024.01); *G05D 2105/10* (2024.01); *G05D 2107/95* (2024.01); *G05D 2111/10* (2024.01)

(58) Field of Classification Search
CPC .. G05D 1/69; G05D 2101/15; G05D 2105/10; G05D 2107/95; G05D 2111/10; G01N 33/0063; G06F 40/20; G06V 10/25
See application file for complete search history.

(56) References Cited

U.S. PATENT DOCUMENTS

| | | | | |
|---|---|---|---|---|
| 10,635,976 B2 * | 4/2020 | Nagasaka | ................. | F01N 3/10 |
| 10,941,687 B2 * | 3/2021 | Muto | ................... | F02B 37/183 |
(Continued)

FOREIGN PATENT DOCUMENTS

| | | |
|---|---|---|
| CN | 106121816 B | 10/2018 |
| CN | 111340280 A | 6/2020 |
(Continued)

OTHER PUBLICATIONS

Kate et al. 'Algorithmic Modeling for Predicting Carbon Emissions in an Individual Vehicles: A Machine Learning and Deep Learning Approach', International Journal of Intelligent Systems and Applications in Engineering, ISSN:2147-67992, https://ijisae.org/index.php/IJISAE/article/view/5487, Mar. 19, 2024, 7 pages.
(Continued)

*Primary Examiner* — Bhavesh V Amin
(74) *Attorney, Agent, or Firm* — CHIP LAW GROUP

(57)     ABSTRACT

Determination and alleviation of root causes for the emission of pollutants from vehicles includes receiving emission data associated with emission of a set of pollutants by the vehicle. The emission data is received from at least one of the vehicle or a set of data sources. A machine learning (ML) model is applied to the emission data. A set of root causes is determined based on the application of the ML model to the emission data. A set of robots is controlled to execute a set of actions within the vehicle to alleviate the set of root causes associated with the emission of the set of pollutants.

20 Claims, 9 Drawing Sheets

(51) Int. Cl.
  *G06F 40/20* (2020.01)
  *G06V 10/25* (2022.01)

(56) References Cited

U.S. PATENT DOCUMENTS

| | | | | |
|---|---|---|---|---|
| 2003/0167139 A1* | 9/2003 | Swartz | | G01R 31/007 |
| | | | | 702/65 |
| 2018/0293814 A1 | 10/2018 | Gilbert et al. | | |
| 2022/0391921 A1* | 12/2022 | Wilner | | G06Q 10/06375 |
| 2023/0115876 A1* | 4/2023 | Avadhani | | G06Q 50/06 |
| | | | | 706/52 |
| 2023/0304430 A1 | 9/2023 | Kempema et al. | | |
| 2023/0325920 A1 | 10/2023 | Moon | | |
| 2023/0385299 A1* | 11/2023 | Al Rasheed | | G06F 16/258 |
| 2024/0037567 A1* | 2/2024 | Nishiwada | | G06Q 50/06 |
| 2024/0037568 A1* | 2/2024 | Nishiwada | | G06Q 50/06 |
| 2024/0144295 A1* | 5/2024 | Nishiwada | | G06Q 30/018 |
| 2024/0161495 A1* | 5/2024 | Gomez | | G06V 10/774 |
| 2024/0225023 A1* | 7/2024 | Killilea | | C12G 1/00 |
| 2025/0013969 A1* | 1/2025 | Sinha | | G06Q 10/06395 |

FOREIGN PATENT DOCUMENTS

| | | | |
|---|---|---|---|
| CN | 114444777 B | 12/2022 | |
| DE | 102018221441 A1 | 6/2020 | |
| FR | 3107979 B1 | 11/2022 | |
| GB | 2603144 A | 8/2022 | |
| IN | 202111007901 A | 5/2021 | |
| IN | 202311057634 A | 9/2023 | |
| JP | 6705540 B1 | 6/2020 | |
| WO | 2023/141102 A1 | 7/2023 | |

OTHER PUBLICATIONS

"Vehicle emissions prediction model", NZ Transport Agency Waka Kotahi, Mar. 6, 2023, 9 pages, doi: https://www.nzta.govt.nz/roads-and-rail/highways-information-portal/technical-disciplines/environment-and-sustainability-in-our-operations/environmental-technical-areas/air-quality/vehicle-emissions-prediction-model#:~:text=The%20Vehicle%20Emissions%20Prediction%20Model,road%2C%20traffic%20and%20operating%20conditions.

International Searching Authority, "Notification of Transmittal of the International Search Report and the Written Opinion of the International Searching Authority, or Declaration," Patent Cooperation Treaty, Dec. 12, 2025, 18 pages, International Application No. PCT/EP2025/077185.

P. Kadam et al., "Prediction Model: CO2 Emission Using Machine Learning," 2018 3rd International Conference for Convergence in Technology (12CT), Pune, India, Apr. 2018, 3 pages, doi: 10.1109/12CT.2018.8529498.

Serafeim G et al., "Machine Learning Models for Prediction of Scope 3 Carbon Emissions", Harvard Business School Accounting & Management Unit Working Paper No. 22-080, Jul. 20, 2022, 36 pages, doi: https://dx.doi.org/10.2139/ssrn.4149874.

Song J et al., "Development of prediction methodology for CO2 emissions and fuel economy of light duty vehicle", Energy, Apr. 1, 2022, 9 pages, vol. 244, Part B, doi: https://doi.org/10.1016/j.energy.2022.123166.

\* cited by examiner

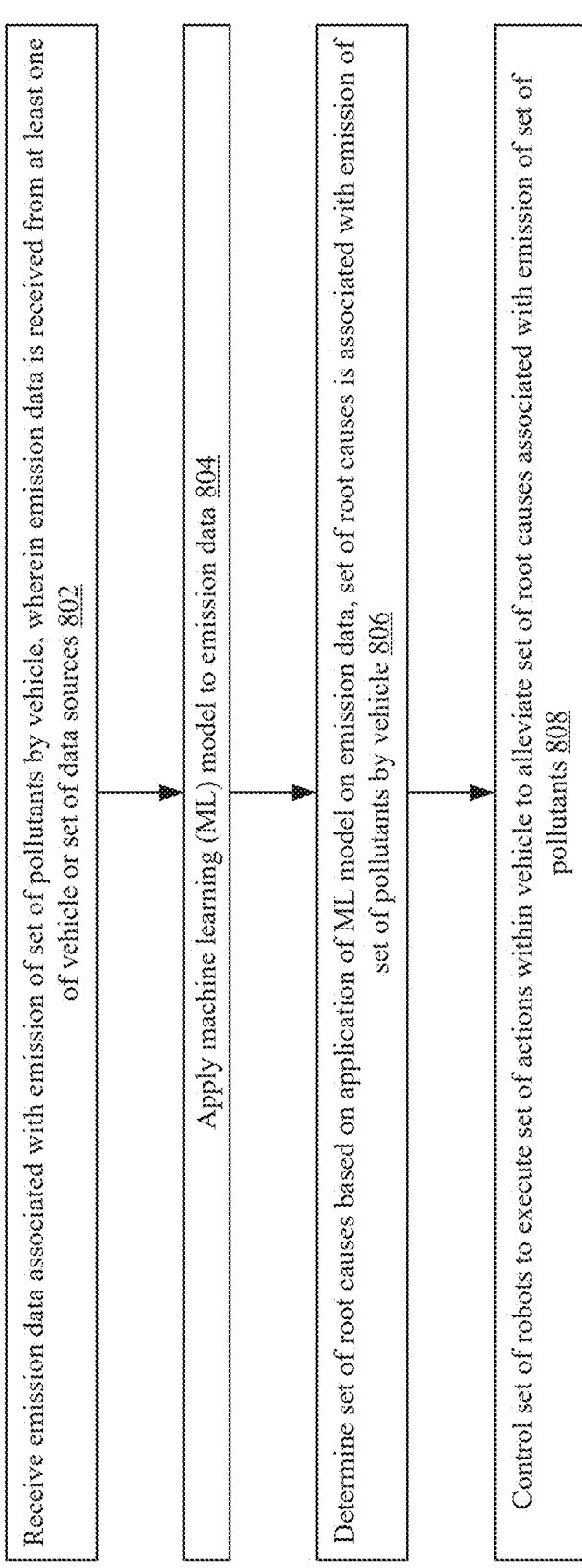

Receive emission data associated with emission of set of pollutants by vehicle, wherein emission data is received from at least one of vehicle or set of data sources 802

Apply machine learning (ML) model to emission data 804

Determine set of root causes based on application of ML model on emission data, set of root causes is associated with emission of set of pollutants by vehicle 806

Control set of robots to execute set of actions within vehicle to alleviate set of root causes associated with emission of set of pollutants 808

DETERMINATION AND ALLEVIATION OF ROOT CAUSES FOR EMISSION OF POLLUTANTS FROM VEHICLES

BACKGROUND

The disclosure relates to the emission of pollutants from vehicles, and more particularly, to the determination and alleviation of root causes for the emission of pollutants from vehicles.

The increasing prevalence of internal combustion engine (ICE) vehicles as well as hybrid ICE vehicles on the road has led to a significant rise in air pollution, as these vehicles are major sources of pollutants such as nitrogen oxides (NOx), carbon monoxide (CO), and particulate matter (PM). These emissions have a detrimental impact on air quality and the environment, exacerbating issues such as smog and respiratory problems in urban areas. To mitigate these effects, regular pollution checks and the timely submission of Pollution Under Control (PUC) certificates are mandated by vehicle authorities. However, non-compliance with these requirements can result in penalties for vehicle owners, highlighting the relevance of adherence to pollution control regulations.

Additionally, emissions from ICE vehicles and hybrid ICE vehicles can be influenced by various operational and environmental factors. For example, low-quality fuel and specific driving conditions, such as idling in traffic jams or operating at low speeds, can increase pollutant emissions. The Engine Control Units (ECUs) in vehicles are designed to adjust engine performance to optimize fuel efficiency and reduce emissions. However, current ECU systems often overcompensate in response to these varying conditions, leading to imbalanced and sometimes elevated emissions.

SUMMARY

According to an embodiment of the disclosure, a computer-implemented method for determination and alleviation of root causes for emission of pollutants from vehicles is described. The computer-implemented method includes receiving, by a computer, emission data associated with an emission of a set of pollutants by the vehicle. The emission data is received from at least one of the vehicle or a set of data sources. The computer-implemented method further includes applying, by the computer, a machine learning (ML) model to the emission data. The computer-implemented method further includes determining, by the computer, a set of root causes based on the application of the ML model to the emission data. The set of root causes is associated with the emission of the set of pollutants by the vehicle. The computer-implemented method further includes controlling, by the computer, a set of robots to execute a set of actions within the vehicle to alleviate the set of root causes associated with the emission of the set of pollutants.

According to one or more embodiments of the disclosure, a system for determination and alleviation of root causes for emission of pollutants from vehicles is described. The system performs a method for determination and alleviation of root causes for emission of pollutants from vehicles. The method includes receiving emission data associated with an emission of a set of pollutants by the vehicle. The emission data is received from at least one of the vehicle or a set of data sources. The method further includes applying a machine learning (ML) model to the emission data. The method further includes determining an emission value indicative of the emission of at least a first pollutant of the set of pollutants. The determination of the emission value is based on the application of the ML model to the emission data. The method further includes determining a set of root causes based on a determination that the emission value is greater than a threshold emission value. The set of root causes is associated with the emission of the set of pollutants by the vehicle. The method further includes controlling a set of robots to execute a set of actions within the vehicle to alleviate the set of root causes associated with the emission of the set of pollutants.

According to one or more embodiments of the disclosure, a computer program product for determination and alleviation of root causes for emission of pollutants from vehicles is described. The computer program product includes one or more computer-readable storage media and program instructions stored on the one or more computer-readable storage media to perform operations including receive emission data associated with an emission of a set of pollutants by the vehicle. The emission data is received from at least one of the vehicle or a set of data sources. The operations further include applying a machine learning (ML) model to the emission data. The operations further include determining a set of root causes based on the application of the ML model to the emission data. The operations further includes controlling a set of robots to execute a set of actions within the vehicle to alleviate the set of root causes associated with the emission of the set of pollutants.

Additional technical features and benefits are realized through the techniques of the disclosure. Embodiments and aspects of the disclosure are described in detail herein and are considered a part of the claimed subject matter. For a better understanding, refer to the detailed description and to the drawings.

BRIEF DESCRIPTION OF THE DRAWINGS

The following description will provide details of preferred embodiments with reference to the following figures wherein:

FIG. 8 is a flowchart that illustrates an exemplary method for determination and alleviation of root causes for emission of pollutants from vehicles, in accordance with an embodiment of the disclosure.

DETAILED DESCRIPTION

Figure 1:
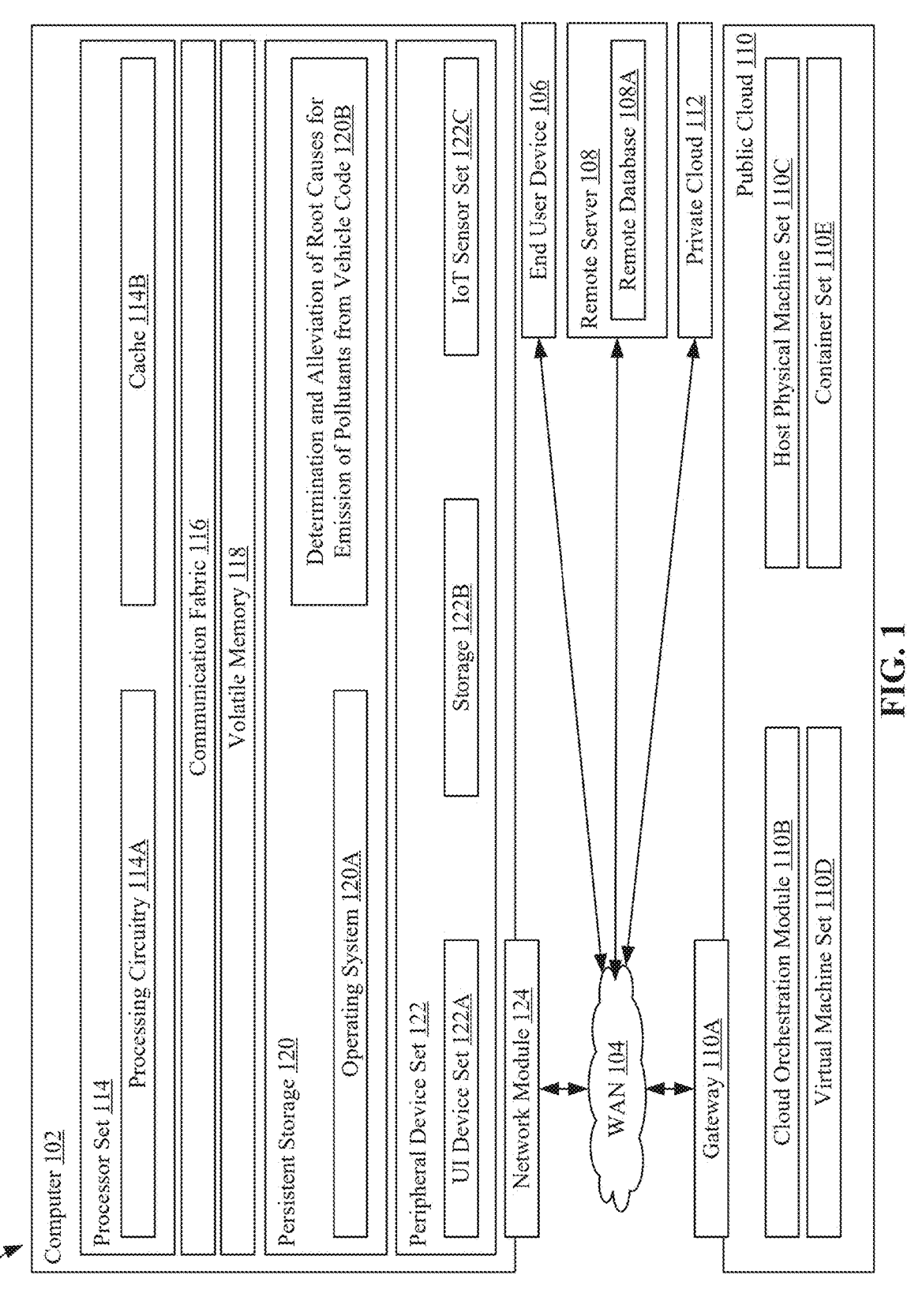
FIG. 1 is a diagram that illustrates a computing environment for the determination and alleviation of root causes for the emission of pollutants from vehicles, in accordance with an embodiment of the disclosure.

With advancements in automotive engineering and decreasing vehicle acquisition costs, the number of internal combustion engine (ICE) vehicles and hybrid ICE vehicles is increasing. These ICE and hybrid ICE vehicles are a major source of air pollution, emitting harmful pollutants such as nitrogen oxides (NOx), carbon monoxide (CO), hydrocarbons (HC), and particulate matter (PM). As the number of ICE vehicles and hybrid ICE vehicles continues to rise globally, the environmental impact of these emissions becomes increasingly severe, contributing to issues like smog, acid rain, and adverse health effects. The challenge of managing these emissions is compounded by several factors that influence the amount and composition of pollutants released into the atmosphere. As the global vehicle fleet expands, so does the environmental impact of these emissions, exacerbating air quality issues and contributing to climate change.

A critical challenge in managing vehicle emissions lies in accurately identifying and addressing the underlying causes that lead to elevated pollutant levels. Current emission control systems often treat the symptoms rather than diagnosing the root causes of high emissions. While existing technologies focus on monitoring and controlling emissions, they may fail to account for the specific conditions or faults within the vehicle that lead to excessive pollution. These root causes could be related to engine malfunctions, sensor failures, or inefficiencies in the emission control systems themselves. Without a precise understanding of these underlying factors, reducing emissions effectively becomes a difficult task.

The disclosure addresses this problem by providing a system that identifies the root causes of elevated emissions in ICE vehicles or hybrid ICE vehicles. The disclosed system goes beyond conventional approaches that merely monitor emission levels. Instead, the disclosed system uses diagnostic tools and machine learning based algorithms to analyze data from various vehicle subsystems, including the engine, exhaust system, and emission control components to determine the root causes behind the elevated emissions. By pinpointing the exact sources of excessive emissions, the system enables targeted interventions to resolve the issues at their origin.

For example, if a vehicle's emissions are higher than expected, the disclosed system is capable of determining whether the cause is a malfunctioning catalytic converter, an exhaust system, or any other issue. Once the root cause is identified, the system transmits instructions to robots to alleviate the root cause so that the emissions are decreased. In case the root cause cannot be solved by the robots, the disclosed system provides corrective actions to address the problem. These actions may include replacing faulty components or unclogging the catalytic converter. By resolving the underlying issues, the system ensures that emissions are reduced to compliant levels, improving the vehicle's environmental performance.

Furthermore, the disclosed system offers a significant advantage by automating the generation of Pollution Under Control (PUC) certifications when emissions are within the prescribed limits. This eliminates the need for vehicle owners to visit PUC centers periodically, saving both time and money. By continuously monitoring emissions and ensuring they remain compliant, the system can issue the required certifications directly to the user and other relevant authorities (such as Transport Offices). Such automation not only streamlines the process but also enhances the overall user experience. The vehicle owners no longer need to worry about missing certification deadlines or facing penalties for non-compliance. The convenience of having emissions monitored and certified in real-time adds value to the user, providing peace of mind and reducing the administrative burden typically associated with PUC renewals.

Furthermore, the disclosed system may improve the operational performance of the vehicle and also increase fuel efficiency which results in a decrease in expenditure of the fuel. Also, the disclosed system reduces global warming and enhances health & economy.

According to an embodiment of the disclosure, a computer-implemented method for determination and alleviation of root causes for emission of pollutants from vehicles is described. The computer-implemented method includes receiving, by a computer, emission data associated with an emission of a set of pollutants by the vehicle. The emission data is received from at least one of the vehicle or a set of data sources. The computer-implemented method further includes applying, by the computer, a machine learning (ML) model to the emission data. The computer-implemented method further includes determining, by the computer, a set of root causes based on the application of the ML model to the emission data. The set of root causes is associated with the emission of the set of pollutants by the vehicle. The computer-implemented method further includes controlling, by the computer, a set of robots to execute a set of actions within the vehicle to alleviate the set of root causes associated with the emission of the set of pollutants.

In other embodiments of the disclosure, the computer-implemented method further includes determining, by the computer, location data indicative of a location of the vehicle. The computer-implemented method further includes obtaining, by the computer, weather data associated with the location of the vehicle based on the location data. The computer-implemented method further includes determining, by the computer, the set of root causes associated with the emission of the set of pollutants by the vehicle based on the application of the ML model to the weather data.

In other embodiments of the disclosure, the computer-implemented method further includes determining, by the computer, the set of robots is capable of executing the set of actions to alleviate the set of root causes. The computer-implemented method further includes generating, by the computer, a set of instructions to control the set of robots to execute the set of actions. The set of instructions is generated based on the determination that the set of robots is capable of executing the set of actions. The computer-implemented method further includes transmitting, by the computer, the set of instructions to the set of robots. The computer-implemented method further includes controlling, by the computer, the set of robots based on the transmission of the set of instructions. The set of robots is controlled to execute the set of actions within the vehicle.

In other embodiments of the disclosure, the computer-implemented method further includes determining, by the computer, the set of robots is incapable of executing the set of actions to alleviate the set of root causes. The computer-implemented method further includes generating, by the computer, a set of recommendations to alleviate the set of root causes for the emission of the set of pollutants by the vehicle. The set of recommendations is generated based on the determination that the set of robots is incapable of executing the set of actions. The computer-implemented method further includes rendering, by the computer, the set of recommendations on at least one of a user device or an infotainment unit associated with the vehicle.

In other embodiments of the disclosure, the set of root causes is associated with a malfunction of a set of components associated with the vehicle. The set of components includes at least one of a catalytic converter associated with the vehicle, an exhaust system associated with the vehicle, a fuel injector associated with the vehicle, a Heating, Ventilation, and Air Conditioning (HVAC) system associated with the vehicle, one or more intake valves associated with the vehicle, an ignition system associated with the vehicle, one or more piston rings associated with the vehicle, or one or more cylinder walls associated with the vehicle.

In other embodiments of the disclosure, the set of root causes includes at least one of a clogging of the catalytic converter, a leakage in the exhaust system, a leakage in the fuel injector, a failure of the HVAC system, a deposition of carbon on the one or more intake valves, a failure of the ignition system, a damage in the one or more piston rings, or a damage in the one or more cylinder walls.

In other embodiments of the disclosure, the set of actions includes at least one of a milling operation on a set of components associated with the vehicle, a fabrication operation of the set of components associated with the vehicle, or a spraying operation on the set of components associated with the vehicle or a repair of the set of components associated with the vehicle.

In other embodiments of the disclosure, the computer-implemented method further includes controlling, by the computer, the set of robots to capture one or more images of a first component of a set of components associated with the vehicle. The first component is associated with a first root cause of the set of root causes. The computer-implemented method further includes determining, by the computer, an area of interest within the first component based on the one or more images. The computer-implemented method further includes controlling, by the computer, a first robot of the set of robots to execute a first action of the set of actions within the area of interest to alleviate the first root cause of the set of root causes.

In other embodiments of the disclosure, the computer-implemented method further includes determining, by the computer, an emission value indicative of the emission of at least a first pollutant of the set of pollutants based on the application of the ML model to the emission data. The computer-implemented method further includes determining, by the computer, the set of root causes for the emission of the set of pollutants by the vehicle. The set of root causes is determined based on a determination that the emission value is greater than a threshold emission value.

In other embodiments of the disclosure, the computer-implemented method further includes determining, by the computer, an emission value indicative of the emission of at least a first pollutant of the set of pollutants. The determination of the emission value is based on the application of the ML model to the emission data. The computer-implemented method further includes generating, by the computer, an emission certificate based on a determination that the emission value is less than a threshold emission value. The computer-implemented method further includes rendering, by the computer, the emission certificate on at least one of a user device, an infotainment unit associated with the vehicle, or an electronic device associated with a transport authority.

In other embodiments of the disclosure, the computer-implemented method further includes applying, by the computer, a language model to the emission data and vehicle data associated with the vehicle. The computer-implemented method further includes generating, by the computer, the emission certificate based on the application of the language model to the emission data and the vehicle data.

In other embodiments of the disclosure, the computer-implemented method further includes obtaining, by the computer, historical emission data associated with the emission of the set of pollutants by a set of vehicles. The computer-implemented method further includes obtaining, by the computer, a historical set of root causes for the emission of the set of pollutants by the set of vehicles. The computer-implemented method further includes generating, by the computer, a training dataset based on the historical emission data and a historical set of root causes. The computer-implemented method further includes training, by the computer, the ML model based on the training dataset.

In other embodiments of the disclosure, the set of robots includes at least one parent robot and at least one child robot, the at least one child robot is associated with the at least one parent robot. At least one robot of the set of robots is docked in an engine of the vehicle.

According to one or more embodiments of the disclosure, a system for determination and alleviation of root causes for emission of pollutants from vehicles is described. The system performs a method for determination and alleviation of root causes for emission of pollutants from vehicles. The method includes receiving emission data associated with an emission of a set of pollutants by the vehicle. The emission data is received from at least one of the vehicle or a set of data sources. The method further includes applying a machine learning (ML) model to the emission data. The method further includes determining an emission value indicative of the emission of at least a first pollutant of the set of pollutants. The determination of the emission value is based on the application of the ML model to the emission data. The method further includes determining a set of root causes based on a determination that the emission value is greater than a threshold emission value. The set of root causes is associated with the emission of the set of pollutants by the vehicle. The method further includes controlling a set of robots to execute a set of actions within the vehicle to alleviate the set of root causes associated with the emission of the set of pollutants.

In other embodiments of the disclosure, the set of root causes is associated with malfunction of a set of components associated with the vehicle. The set of components includes at least one of a catalytic converter associated with the vehicle, an exhaust system associated with the vehicle, a fuel injector associated with the vehicle, a Heating, Ventilation, and Air Conditioning (HVAC) system associated with the vehicle, one or more intake valves associated with the vehicle, an ignition system associated with the vehicle, one or more piston rings associated with the vehicle, or one or more cylinder walls associated with the vehicle.

In other embodiments of the disclosure, the set of root causes includes at least one of a clogging of the catalytic converter, a leakage in the exhaust system, a leakage in the fuel injector, a failure of the HVAC system, a deposition of carbon on the one or more intake valves, a failure of the ignition system, a damage in the one or more piston rings, or a damage in the one or more cylinder walls.

In other embodiments of the disclosure, the set of actions includes at least one of a milling operation on a set of components associated with the vehicle, a fabrication operation of the set of components associated with the vehicle, or a spraying operation on the set of components associated with the vehicle or a repair of the set of components associated with the vehicle.

In other embodiments of the disclosure, the system further determines the set of robots are able to execute the set of actions to alleviate the set of root causes. The system further generates a set of instructions to control the set of robots to execute the set of actions. The set of instructions is generated based on the determination that the set of robots is able to execute the set of actions to alleviate the set of root causes. The system further transmits the set of instructions to the set of robots. The system further controls the set of robots based on the transmission of the set of instructions. The set of robots is controlled to execute the set of actions within the vehicle.

In other embodiments of the disclosure, the system further determines the set of robots is unable to execute the set of actions to alleviate the set of root causes. The system further generates a set of recommendations to alleviate the set of root causes for the emission of the set of pollutants by the vehicle. The set of recommendations is generated based on the determination that the set of robots is unable to execute the set of actions to alleviate the set of root causes. The system further renders the set of recommendations on at least one of a user device or an infotainment unit associated with the vehicle.

According to one or more embodiments of the disclosure, a computer program product for determination and alleviation of root causes for emission of pollutants from vehicles is described. The computer program product includes one or more computer-readable storage media and program instructions stored on the one or more computer-readable storage media to perform operations including receive emission data associated with an emission of a set of pollutants by the vehicle. The emission data is received from at least one of the vehicle or a set of data sources. The operations further include applying a machine learning (ML) model to the emission data. The operations further include determining a set of root causes based on the application of the ML model to the emission data. The operations further include controlling a set of robots to execute a set of actions within the vehicle to alleviate the set of root causes associated with the emission of the set of pollutants.

Various aspects of the disclosure are described by narrative text, flowcharts, block diagrams of computer systems, and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated operation, concurrently, or in a manner at least partially overlapping in time.

A computer program product embodiment ("CPP embodiment" or "CPP") is a term used in the disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer-readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer-readable storage medium, as that term is used in the disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation, or garbage collection, but this does not render the storage device as transitory because the data is not transitory while it is stored.

FIG. 1 is a diagram that illustrates a computing environment for determination and alleviation of root causes for emission of pollutants from vehicles, in accordance with an embodiment of the disclosure. With reference to FIG. 1, there is shown a computing environment 100 that contains an example of an environment for the execution of at least some of the computer code involved in performing the disclosed methods, such as a determination and alleviation of root causes for emission of pollutants from vehicle code 120B. In addition to the determination and alleviation of root causes for emission of pollutants from vehicle code 120B, computing environment 100 includes, for example, a computer 102, a wide area network (WAN) 104, an end user device (EUD) 106, a remote server 108, a public cloud 110, and a private cloud 112. In this embodiment of the disclosure, the computer 102 includes a processor set 114 (including a processing circuitry 114A and a cache 114B), a communication fabric 116, a volatile memory 118, a persistent storage 120 (including an operating system 120A and the determination and alleviation of root causes for emission of pollutants from vehicle code 120B, as identified above), a peripheral device set 122 (including a user interface (UI) device set 122A, a storage 122B, and an Internet of Things (IoT) sensor set 122C), and a network module 124. The remote server 108 includes a remote database 108A. The public cloud 110 includes a gateway 110A, a cloud orchestration module 110B, a host physical machine set 110C, a virtual machine set 110D, and a container set 110E.

The computer 102 may take the form of a desktop computer, a laptop computer, a tablet computer, a smartphone, a smartwatch or other wearable computer, a mainframe computer, a quantum computer, or any other form of a computer or a mobile device now known or to be developed in the future that is capable of running a program, accessing a network or querying a database, such as a remote database 108A. As is well understood in the art of computer technology, and depending upon the technology, the performance of a computer-implemented method may be distributed among multiple computers and/or between multiple locations. On the other hand, in this presentation of the computing environment 100, detailed discussion is focused on a single computer, specifically the computer 102, to keep the presentation as simple as possible. The computer 102 may be located in a cloud, even though it is not shown in a cloud in FIG. 1. On the other hand, computer 102 is not required to be in a cloud except to any extent as may be affirmatively indicated.

The processor set 114 includes one, or more, computer processors of any type now known or to be developed in the future. The processing circuitry 114A may be distributed over multiple packages, for example, multiple, coordinated integrated circuit chips. The processing circuitry 114A may implement multiple processor threads and/or multiple processor cores. The cache 114B may be memory that is located in the processor chip package(s) and is typically used for data or code that should be available for rapid access by the threads or cores running on the processor set 114. Cache memories are typically organized into multiple levels depending upon relative proximity to the processing circuitry 114A. Alternatively, some, or all, of the cache 114B for the processor set 114 may be located "off-chip." In some computing environments, the processor set 114 may be designed for working with qubits and performing quantum computing.

Computer readable program instructions are typically loaded onto the computer 102 to cause a series of operations to be performed by the processor set 114 of the computer 102 and thereby effect a computer-implemented method, such that the instructions thus executed will instantiate the methods specified in flowcharts and/or narrative descriptions of computer-implemented methods included in this document (collectively referred to as "the disclosed methods"). These computer-readable program instructions are stored in various types of computer-readable storage media, such as the cache 114B and the other storage media discussed below. The program instructions, and associated data, are accessed by the processor set 114 to control and direct the performance of the disclosed methods. In computing environment 100, at least some of the instructions for performing the disclosed methods may be stored in the dynamic modification of the determination and alleviation of root causes for emission of pollutants from vehicle code 120B in persistent storage 120.

The communication fabric 116 is the signal conduction path that allows the various components of computer 102 to communicate with each other. Typically, this fabric is made of switches and electrically conductive paths, such as the switches and electrically conductive paths that make up buses, bridges, physical input/output ports, and the like. Other types of signal communication paths may be used, such as fiber optic communication paths and/or wireless communication paths.

The volatile memory 118 is any type of volatile memory now known or to be developed in the future. Examples include dynamic type random access memory (RAM) or static type RAM. Typically, the volatile memory 118 is characterized by a random access, but this is not required unless affirmatively indicated. In the computer 102, the volatile memory 118 is located in a single package and is internal to computer 102, but alternatively or additionally, the volatile memory 118 may be distributed over multiple packages and/or located externally with respect to computer 102.

The persistent storage 120 is any form of non-volatile storage for computers that is now known or to be developed in the future. The non-volatility of this storage means that the stored data is maintained regardless of whether power is being supplied to computer 102 and/or directly to the persistent storage 120. The persistent storage 120 may be a read-only memory (ROM), but typically at least a portion of the persistent storage 120 allows writing of data, deletion of data, and re-writing of data. Some familiar forms of the persistent storage 120 include magnetic disks and solid-state storage devices. The operating system 120A may take several forms, such as various known proprietary operating systems or open-source Portable Operating System Interface-type operating systems that employ a kernel. The code included in the determination and alleviation of root causes for emission of pollutants from vehicle code 120B typically includes at least some of the computer code involved in performing the disclosed methods.

The peripheral device set 122 includes the set of peripheral devices of computer 102. Data communication connections between the peripheral devices and the other components of computer 102 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments of the disclosure, the UI device set 122A may include components such as a display screen, speaker, microphone, wearable devices (such as goggles and smartwatches), keyboard, mouse, printer, touchpad, game controllers, and haptic devices. The storage 122B is external storage, such as an external hard drive, or insertable storage, such as an SD card. The storage 122B may be persistent and/or volatile. In some embodiments of the disclosure, storage 122B may take the form of a quantum computing storage device for storing data in the form of qubits. In embodiments of the disclosure where computer 102 is required to have a large amount of storage (for example, where computer 102 locally stores and manages a large database) then this storage may be provided by peripheral storage devices designed for storing very large amounts of data, such as a storage area network (SAN) that is shared by multiple, geographically distributed computers. The IoT sensor set 122C is made up of sensors that can be used in Internet of Things applications. For example, one sensor may be a thermometer, and another sensor may be a motion detector.

The network module 124 is the collection of computer software, hardware, and firmware that allows computer 102 to communicate with other computers through WAN 104. The network module 124 may include hardware, such as modems or Wi-Fi signal transceivers, software for packetizing and/or de-packetizing data for communication network transmission, and/or web browser software for communicating data over the internet. In some embodiments of the disclosure, network control functions, and network forwarding functions of the network module 124 are performed on the same physical hardware device. In other embodiments of the disclosure (for example, embodiments that utilize software-defined networking (SDN)), the control functions and the forwarding functions of the network module 124 are performed on physically separate devices, such that the control functions manage several different network hardware devices. Computer-readable program instructions for performing the disclosed methods can typically be downloaded to computer 102 from an external computer or external storage device through a network adapter card or network interface included in the network module 124.

The WAN 104 is any wide area network (for example, the internet) capable of communicating computer data over non-local distances by any technology for communicating computer data, now known or to be developed in the future. In some embodiments of the disclosure, the WAN 104 may be replaced and/or supplemented by local area networks (LANs) designed to communicate data between devices located in a local area, such as a Wi-Fi network. The WAN 104 and/or LANs typically include computer hardware such as copper transmission cables, optical transmission fibers, wireless transmission, routers, firewalls, switches, gateway computers, and edge servers.

The EUD 106 is any computer system that is used and controlled by an end user (for example, a customer of an enterprise that operates computer 102) and may take any of the forms discussed above in connection with computer 102. The EUD 106 typically receives helpful and useful data from the operations of computer 102. For example, in a hypothetical case where computer 102 is designed to provide a recommendation to an end user, this recommendation would typically be communicated from the network module 124 of computer 102 through WAN 104 to EUD 106. In this way, the EUD 106 can display, or otherwise present recommendations to an end user. In some embodiments of the disclosure, EUD 106 may be a client device, such as a thin client, heavy client, mainframe computer, desktop computer, and so on.

The remote server 108 is any computer system that serves at least some data and/or functionality to the computer 102. The remote server 108 may be controlled and used by the same entity that operates the computer 102. The remote server 108 represents the machine(s) that collect and store helpful and useful data for use by other computers, such as the computer 102. For example, in a hypothetical case where the computer 102 is designed and programmed to provide a recommendation based on historical data, then this historical data may be provided to the computer 102 from the remote database 108A of the remote server 108.

The public cloud 110 is any computer system available for use by multiple entities that provides on-demand availability of computer system resources and/or other computer capabilities, especially data storage (cloud storage) and computing power, without direct active management by the user. Cloud computing typically leverages the sharing of resources to achieve coherence and economics of scale. The direct and active management of the computing resources of the public cloud 110 is performed by the computer hardware and/or software of the cloud orchestration module 110B. The computing resources provided by the public cloud 110 are typically implemented by virtual computing environments that run on various computers making up the computers of the host physical machine set 110C, which is the universe of physical computers in and/or available to the public cloud 110. The virtual computing environments (VCEs) typically take the form of virtual machines from the virtual machine set 110D and/or containers from the container set 110E. It is understood that these VCEs may be stored as images and may be transferred among and between the various physical machine hosts, either as images or after the instantiation of the VCE. The cloud orchestration module 110B manages the transfer and storage of images, deploys new instantiations of VCEs, and manages active instantiations of VCE deployments. The gateway 110A is the collection of computer software, hardware, and firmware that allows public cloud 110 to communicate through WAN 104.

Some further explanation of virtualized computing environments (VCEs) will now be provided. VCEs can be stored as "images". A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

The private cloud 112 is similar to public cloud 110, except that the computing resources are only available for use by a single enterprise. While the private cloud 112 is depicted as being in communication with the WAN 104, in other embodiments of the disclosure, a private cloud may be disconnected from the internet entirely and only accessible through a local/private network. A hybrid cloud is a composition of multiple clouds of different types (for example, private, community, or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment of the disclosure, the public cloud 110 and the private cloud 112 are both part of a larger hybrid cloud.

Figure 2:
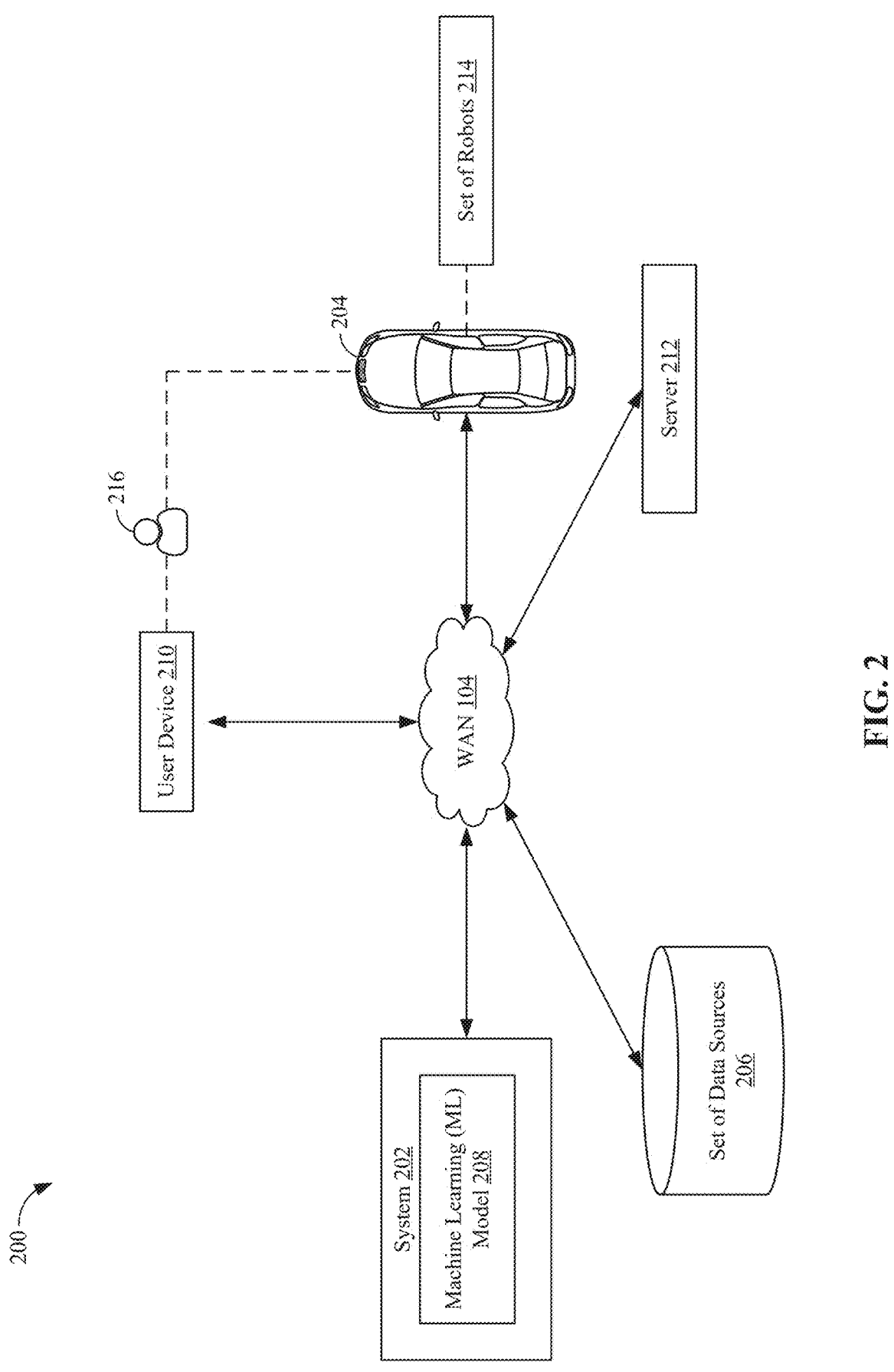
FIG. 2 is a diagram that illustrates an environment for the determination and alleviation of root causes for the emission of pollutants from vehicles, in accordance with an embodiment of the disclosure.

FIG. 2 is a diagram that illustrates an environment for the determination and alleviation of root causes for the emission of pollutants from vehicles, in accordance with an embodiment of the disclosure. FIG. 2 is explained in conjunction with elements from FIG. 1. With reference to FIG. 2, there is shown a diagram of a network environment 200. The network environment 200 includes a system 202, a vehicle 204, one or more data sources 206, a machine learning (ML) model 208, a user device 210, a server 212, and a set of robots 214. The network environment 200 further includes an entity 216 associated with the user device 210. The network environment 200 further includes the WAN 104 of FIG. 1. In an embodiment of the disclosure, the user device 210 may be an exemplary embodiment of the EUD 106. Similarly, the system 202 may be an exemplary embodiment of the computer 102 in FIG. 1.

The system 202 may include suitable logic, circuitry, interfaces, and/or code that may be configured for the determination and alleviation of root causes for the emission of pollutants from vehicles. The system 202 may be configured to receive emission data associated with an emission of a set of pollutants by the vehicle 204. The emission data may be received from at least one of the vehicle 204 or the set of data sources 206. The system 202 may be configured to apply the ML model 208 to the emission data. The system 202 may be further configured to determine a set of root causes associated with the emission of the set of pollutants by the vehicle based on the application of the ML model 208 to the emission data. The system 202 may be further configured to control the set of robots 214 to execute a set of actions within the vehicle 204 to alleviate the set of root causes associated with the emission of the set of pollutants. Examples of the system 202 may include, but are not limited to, a server, a computing device, an engine control unit (ECU), a virtual computing device, a mainframe machine, a computer workstation, a smartphone, a cellular phone, a mobile phone, a gaming device, or a consumer electronic (CE) device.

The vehicle 204 may be a non-autonomous vehicle, a semi-autonomous vehicle, or a fully autonomous vehicle, for example, as defined by the National Highway Traffic Safety Administration (NHTSA). Examples of the vehicle 204 may include, but are not limited to, a two-wheeler vehicle, a three-wheeler vehicle, a four-wheeler vehicle, or a vehicle with autonomous drive capability that uses one or more distinct non-renewable power sources. The vehicle 204 may be a system through which an occupant (for example rider) may travel from a start point to a destination point. Examples of the two-wheeler vehicle may include, but are not limited to, an internal combustion engine (ICE)-based two-wheeler. Similarly, examples of the four-wheeler vehicle may include, but are not limited to, an internal combustion engine (ICE)-based or a hybrid ICE car. It may be noted here that the block diagram of the vehicle 204 is merely shown as an example in FIG. 2. The present disclosure may be also applicable to other structures, designs, or shapes of the vehicle 204. The description of other types of the vehicle and respective structures, designs, or shapes has been omitted from the disclosure for the sake of brevity.

Each of the set of data sources 206 may correspond to an organized collection of data that may be stored and accessed electronically from a computer system (such as the system 202). Each of the set of data sources 206 may be designed to manage, store, retrieve, and update data efficiently. In an exemplary implementation, each data source of the set of data sources 206 may correspond to a database. In such an implementation, the structure of each database typically involves tables, records, and fields that can be managed through various database management systems (DBMS). Examples of each data source of the set of data sources 206 may include, but are not limited to, a relational database, a Non-Structured Query Language (SQL) database, a hierarchical database, a network database, a transactional database, a data warehouse, and a distributed database.

The ML model 208 may be a computational network or a system of artificial neurons, arranged in a plurality of layers, as nodes. The plurality of layers of the ML model 208 may include an input layer, one or more hidden layers, and an output layer. Each layer of the plurality of layers may include one or more nodes (or artificial neurons). Outputs of all nodes in the input layer may be coupled to at least one node of the hidden layer(s). Similarly, inputs of each hidden layer may be coupled to outputs of at least one node in other layers of the ML model 208. Outputs of each hidden layer may be coupled to inputs of at least one node in other layers of the ML model 208. Node(s) in the final layer may receive inputs from at least one hidden layer to output a result. The number of layers and the number of nodes in each layer may be determined from the hyper-parameters of the ML model 208. Such hyper-parameters may be set before or while training the ML model 208 on a training dataset.

Each node of the ML model 208 may correspond to a mathematical function (e.g., a sigmoid function or a rectified linear unit) with a set of parameters, tunable during the training of the network. The set of parameters may include, for example, a weight parameter, a regularization parameter, and the like. Each node may use the mathematical function to compute an output based on one or more inputs from nodes in other layer(s) (e.g., previous layer(s)) of the ML model 208. All or some of the nodes of the ML model 208 may correspond to the same or a different mathematical function.

In training the ML model 208, one or more parameters of each node of the ML model 208 may be updated based on whether an output of the final layer for a given input (from the training dataset) matches a correct result based on a loss function for the ML model 208. The above process may be repeated for the same or a different input until a minimum of the loss function may be achieved, and a training error may be minimized. Several methods for training are known in the art, for example, gradient descent, stochastic gradient descent, batch gradient descent, gradient boost, meta-heuristics, and the like.

The ML model 208 may include electronic data, such as, for example, a software program, code of the software program, libraries, applications, scripts, or other logic or instructions for execution by a processing device, such as a processor set. The ML model 208 may include code and routines configured to enable a computing device, such as the system 202, to perform one or more operations. Additionally, or alternatively, the ML model 208 may be implemented using hardware including a processor, a microprocessor (e.g., to perform or control the performance of one or more operations), a field-programmable gate array (FPGA), or an application-specific integrated circuit (ASIC). Alternatively, in some embodiments, the ML model 208 may be implemented using a combination of hardware and software. Although in FIG. 2, the ML model 208 is shown as integrated within the system 202, the disclosure is not so limited. Accordingly, in some embodiments, the ML model 208 may be a separate entity from the system 202, without deviation from the scope of the disclosure. In an embodiment, the ML model 208 may be stored in the server 212. Examples of the ML model 208 may include, but are not limited to, a deep neural network (DNN), a convolutional neural network (CNN), a CNN-recurrent neural network (CNN-RNN), an artificial neural network (ANN), a fully connected neural network, and/or a combination of such networks.

The user device 210 may include suitable logic, circuitry, interfaces, and/or code that may be configured to render a message or a set of recommendations received from the system 202 on a display screen associated with the user device 210. In an embodiment, the user device 210 may include a display screen. In an embodiment, the user device 210 may be associated with the entity 216. The entity 216 may correspond to a stand-alone user or an organization. Examples of the user device 210 may include, but are not limited to, a computing device, a mainframe machine, a server, a computer work-station, a smartphone, a cellular phone, a mobile phone, a gaming device, a consumer electronic (CE) device, a head-mounted device, a Virtual Reality (VR) Headset, an Augmented Reality (AR) Device, a Mixed Reality (MR) Device, a Projection-based System, and/or any other device with computer vision display capabilities.

The display screen may include suitable logic, circuitry, and interfaces that may be configured to render the message or the set of recommendations. In some embodiments of the disclosure, the display screen may be an external display device associated with the user device 210. The display screen may be a touch screen which may enable the entity 216 to provide an input via the display screen. The touch screen may be at least one of a resistive touch screen, a capacitive touch screen, or a thermal touch screen. In an embodiment, the display screen may refer to a display screen of a head-mounted device (HMD), a smart-glass device, a see-through display, a projection-based display, an electro-chromic display, or a transparent display. In some embodiments of the disclosure, the display screen may be realized through several known technologies such as, but are not limited to, at least one of a Liquid Crystal Display (LCD) display, a Light Emitting Diode (LED) display, a plasma display, or an Organic LED (OLED) display technology, or other display devices.

The server 212 may include suitable logic, circuitry, interfaces, and/or code that may be configured to store the emission data, the set of root causes, the set of actions, the set of instructions, and the set of recommendations. The server 212 may be configured to store the ML model 208 and a language model. The server 212 may be implemented as a cloud server and may execute operations through web applications, cloud applications, HTTP requests, repository operations, file transfer, and the like. Other example implementations of the server 212 may include, but are not limited to, a database server, a file server, a web server, a media server, an application server, a mainframe server, or a cloud computing server.

In an embodiment of the disclosure, the server 212 may be implemented as a plurality of distributed cloud-based resources by use of several technologies that are well known to those ordinarily skilled in the art. A person with ordinary skill in the art will understand that the scope of the disclosure may not be limited to the implementation of the server 212 and the system 202 as two separate entities. In certain embodiments, the functionalities of the server 212 can be incorporated in its entirety or at least partially in the system 202, without a departure from the scope of the disclosure.

Each robot of the set of robots 214 may include suitable logic, circuitry, interfaces, and/or code that may be configured to perform the set of actions autonomously. Each robot of the set of robots 214 may be designed to interact with its environment, execute pre-programmed actions, and make real-time decisions based on sensor inputs. Depending on their purpose, each robot of the set of robots 214 may be configured to carry out complex operations such as milling, fabrication, and spraying. In an embodiment, each robot of the set of robots 214 may be a miniature robots docked in the engine of the vehicle 204. Each robot of the set of robots 214 may be configured to continuously monitor an Electronic Control Unit (ECU) of the vehicle 204 in real-time. In case of abnormalities where the emission value indicative of the emission of at least a first pollutant of the set of pollutants is greater than a threshold emission value, the system 202 may provide a set of instructions in a message queue from which each robot of the set of robots takes a command, triggers an action, and apply a fix in real-time. Examples of each robot of the set of robots 214 may include, but are not limited to, an industrial robot, an autonomous robot, a service robot, or a mobile robot.

In operation, the system 202 may be configured to receive the emission data associated with the emission of the set of pollutants by the vehicle 204. The set of pollutants emitted by the vehicle 204 may include various harmful substances released during the combustion of fuel in an engine of the vehicle 204, contributing to air pollution and posing significant health and environmental risks. Such a set of pollutants typically include Carbon Monoxide (CO), a colorless and toxic gas formed from incomplete fuel combustion, and Nitrogen Oxides (NOx), which contribute to smog, acid rain, and respiratory problems. In some embodiments, the vehicle 204 may also emit Particulate Matter (PM), tiny particles that can penetrate the lungs and bloodstream, causing serious health issues. Hence, the set of pollutants may include, but is not limited to, Carbon Monoxide (CO), Nitrogen Oxides (NOx), and Particulate Matter (PM). In an embodiment, the system 202 may receive the emission data from the vehicle 204. Specifically, the system 202 may receive the emission data from a set of sensors that may be integrated within or associated with the vehicle 204. In an alternate embodiment, the system 202 receives the emission data from the set of data sources 206.

The system 202 may be further configured to apply the ML model 208 to the received emission data. The ML model 208 may be a pre-trained model that may be trained to determine the set of root causes associated with the emission of the set of pollutants by the vehicle 204. Based on the application of the ML model 208 to the emission data, the system 202 may be configured to determine the set of root causes associated with the emission of the set of pollutants by the vehicle 204. Details about the set of root causes are provided, for example, in FIG. 3.

Based on the determination of the set of root causes, the system 202 may be configured to control the set of robots 214 to execute a set of actions within the vehicle 204 to alleviate the set of root causes associated with the emission of the set of pollutants by the vehicle. Details about the set of actions are provided, for example, in FIG. 3, and FIG. 6.

Figure 3:
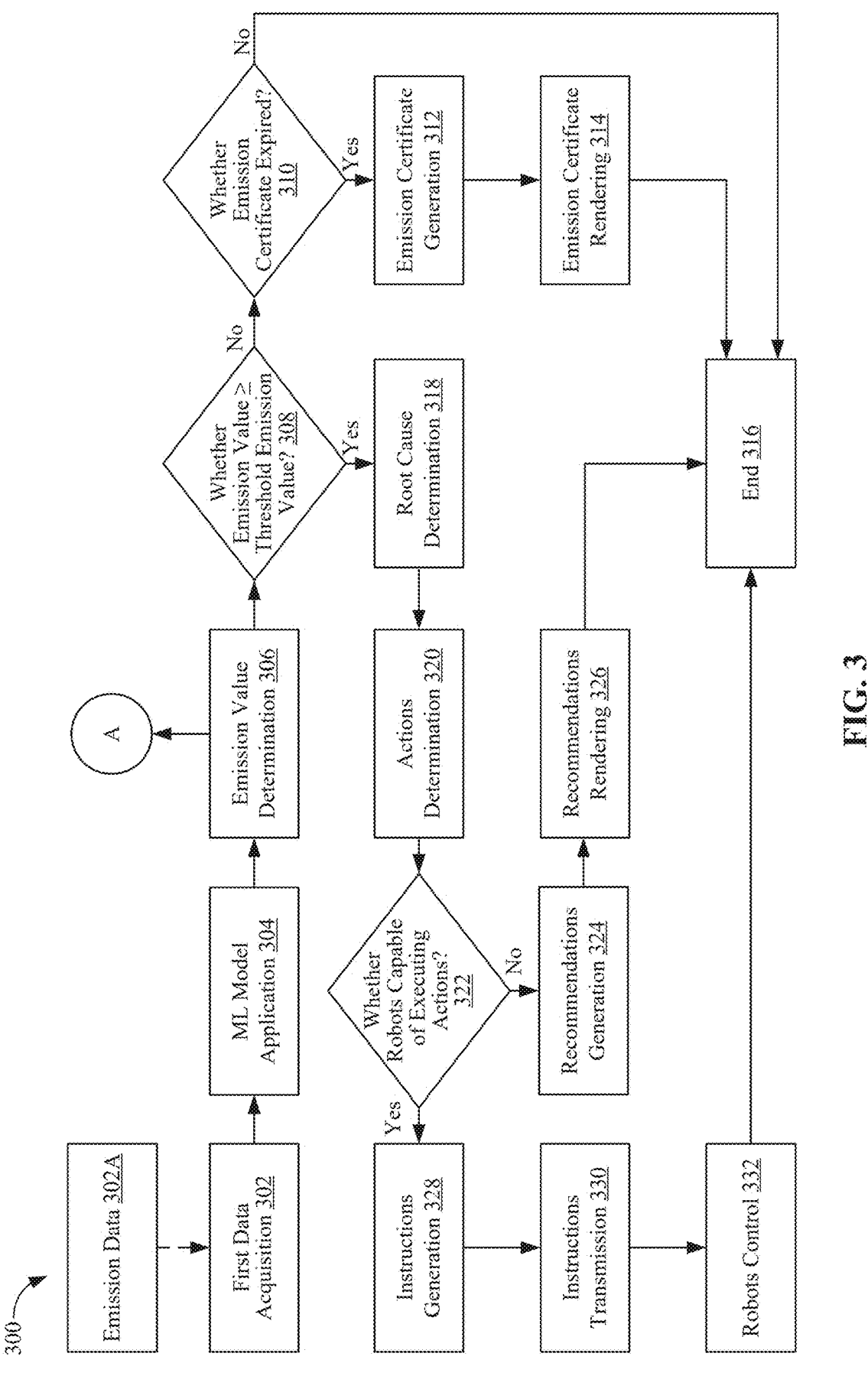
FIG. 3 is a diagram that illustrates exemplary operations determination and alleviation of root causes for the emission of pollutants from vehicles, in accordance with an embodiment of the disclosure.

FIG. 3 is a diagram that illustrates exemplary operations determination and alleviation of root causes for the emission of pollutants from vehicles, in accordance with an embodiment of the disclosure. FIG. 3 is explained in conjunction with elements from FIG. 1, and FIG. 2. With reference to FIG. 3, there is shown a block diagram 300 that illustrates exemplary operations from 302 to 332, as described herein. The exemplary operations illustrated in the block diagram 300 may start at 302 and may be performed by any computing system, apparatus, or device, such as by the computer 102 of FIG. 1 or system 202 of FIG. 2. Although illustrated with discrete blocks, the exemplary operations associated with one or more blocks of the block diagram 300 may be divided into additional blocks, combined into fewer blocks, or eliminated, depending on the particular implementation. The operations from 302 to 332 may be executed as soon as the ignition of the vehicle 204 may be turned on.

At 302, a data acquisition operation may be executed. In the first data acquisition operation, the system 202 may be configured to receive the emission data associated with the emission of the set of pollutants by the vehicle 204. As discussed above, the vehicle 204 with an internal combustion engine (ICE) or hybrid ICE may emit a set of pollutants that may include Carbon Monoxide (CO), Carbon dioxide ($CO_2$), Nitrogen Oxides (NOx), hydrocarbons, and Particulate Matter (PM). In an embodiment, the emission data may be indicative of the amount of each pollutant that may be emitted by the vehicle in the environment and may be expressed in grams per kilometer (g/km).

In an embodiment, the system 202 may be configured to receive the emission data from the vehicle 204. Specifically, a set of sensors may be embedded within the vehicle 204.

Each sensor of the set of sensors may be configured to capture the emission data associated with at least one pollutant of the set of pollutants and transmit the captured emission data to the ECU of the vehicle 204. The ECU of the vehicle 204 may be further configured to receive the emission data from the set of sensors and further transmit the received emission data to the system 202.

In an alternate embodiment, the system 202 may be configured to receive the emission data from the set of data sources 206. In such an embodiment, the set of sensors may be configured to capture the emission data and transmit the captured emission data to at least one data source of the set of data sources 206. The at least one data source may be associated with the set of sensors or the vehicle 204. By way of example and not limitation, the set of data sources 206 may correspond to a set of databases associated with the set of sensors or the vehicle 204 where the captured emission data may be stored. In such an embodiment, the system 202 may receive the emission data from the set of data sources 206 using one or more data reception (or retrieval) techniques (such as application programming interface (API) calls) known in the art.

In addition to the emission data, the system 202 may be further configured to obtain weather data associated with a location of the vehicle 204. To obtain the weather data, the system 202 may be further configured to receive location data indicative of the location of the vehicle 204. In an embodiment, the location data may be received from a location sensor that may be associated with or integrated within the vehicle 204. Based on the received location data, the system 202 may be configured to obtain the weather information indicative of the weather at the location of the vehicle 204.

The weather information may refer to data and reports about the current and forecasted atmospheric conditions in the location of the vehicle 204. The weather information may typically include various meteorological parameters such as temperature, humidity, wind speed and direction, precipitation, cloud cover, atmospheric pressure, and visibility at the location of the vehicle 204.

At 304, an ML model application operation may be executed. In the ML model application operation, the system 202 may be configured to apply the ML model 208 to the emission data. As discussed above, the ML model 208 may be a pre-trained model that may be trained to determine an emission value that may be indicative of the emission of at least a first pollutant of the set of pollutants. Specifically, the emission value may refer to a concentration of corresponding pollutant (say CO gas) in the exhaust gases emitted by a vehicle, expressed as a percentage of the total volume of exhaust gases or in parts per million. For example, if the emission value corresponds to "CO emission=0.3%", then it may indicate that the concentration of carbon monoxide (CO) in the exhaust gases emitted by the vehicle 204. As another example, if the emission value corresponds to "HC emission=200 ppm", then it may indicate that for everyone million units of exhaust gas, 200 units consist of hydrocarbons.

At 306, an emission value determination operation may be executed. In the emission value determination operation, the system 202 may be configured to determine the emission value based on the application of the ML model 208 to the emission data. As discussed above, the emission value may refer to a concentration of the corresponding pollutant (say CO gas) in the exhaust gases emitted by the vehicle 204. In an embodiment, the ML model 208 may be pre-trained to output the emission value indicative of the emission of at least a first pollutant of the set of pollutants.

At 308, it may be determined whether the emission value is greater than (or equal to) a threshold emission value. In case the emission value is greater than or equal to the threshold emission value, the control may be transferred to 318. Alternatively, if the emission value is less than the threshold emission value, the control may be transferred to 310. In an embodiment, the threshold emission value refers to a predefined limit or a benchmark for an amount of pollutants that the vehicle 204 may legally or acceptably emit. This value may be determined by regulatory authorities, such as environmental agencies or government bodies, to ensure that emissions remain within levels that minimize environmental and health impacts.

At 310, it may be determined whether a current pollution emission certificate associated with the vehicle has expired or not. If it is determined that the pollution emission certificate has expired, the control may be transferred to 312. Alternatively, if it is determined that the pollution emission certificate has not expired, control may be transferred to end at 316. In an embodiment, the pollution emission certificate (or an emission certificate) is a document issued by an authorized entity that certifies a vehicle's emissions are within the prescribed environmental standards set by the regulatory authorities. The pollution emission certificate serves as proof that the corresponding vehicle has undergone an emissions test and that the measured emission levels are within legally permissible limits for pollutants such as carbon oxides ($CO_x$), nitrogen oxides ($NO_x$), particulate matter (PM), and hydrocarbons (HC).

Typically, the pollution emission certificate includes details about the vehicle, such as its make, model, engine type, and registration number, along with the measured levels of various pollutants emitted by the vehicle (such as the vehicle 204). It also specifies the certification period, which indicates the validity of the certificate, after which the vehicle must undergo a new emissions test. The certificate is issued by the organization or agency responsible for conducting the test and is often required by law for vehicle registration, renewal, or continued operation, ensuring compliance with regulations aimed at reducing air pollution.

At 312, an emission certificate generation operation may be executed. In the emission certificate generation operation, the system 202 may be configured to generate an emission certificate based on the determined emission values. In an embodiment, the system 202 may apply a language model to the emission data and vehicle data associated with the vehicle to generate the emission certificate. Details about the generation of the emission certificate are provided, for example, in FIG. 4.

At 314, an emission certificate rendering operation may be executed. In the emission certificate rendering operation, the system 202 may render the emission certificate on at least one of the user device 210, an infotainment unit associated with the vehicle 204, or an electronic device associated with the regulatory authorities (such as a transport authority). The infotainment unit associated with the vehicle refers to an integrated system within the vehicle 204 that combines information delivery and entertainment functionalities. This device typically includes features such as, but not limited to, a display screen, navigation, multimedia playback (audio and video), smartphone connectivity, internet access, and vehicle diagnostics. It may also provide access to real-time information like traffic updates, weather reports, and safety alerts, enhancing the driving experience by offering both convenience and entertainment. In an embodiment, the rendering of the emission certificate on the infotainment unit may correspond to the displaying of a message indicating that the emission certificate is generated on the display screen. In an embodiment, the electronic device associated with the regulatory authorities may correspond to a server associated with the regulatory authorities. In such a case, the rendering of the emission certificate may correspond to the storage of the emission certificate in the server associated with the regulatory authorities (such as the Department of Transportation).

At 318, a root cause determination operation may be executed. In the root cause determination operation, the system 202 may be configured to determine a set of root causes that may be associated with the emission of the set of pollutants by the vehicle 204. In an embodiment, the set of root causes may refer to the underlying factors, conditions, or issues that directly contribute to the emission of pollutants by the vehicle 204. Such a set of root causes may be the fundamental sources of the problem, as opposed to symptoms or secondary effects, and addressing them is vital for effectively reducing the emission from the vehicle 204.

In an embodiment, the set of root causes may be associated with a malfunction of the set of components associated with the vehicle 204. In an embodiment, the set of components may include, but are not limited to, a catalytic converter associated with the vehicle 204, an exhaust system associated with the vehicle 204, a fuel injector associated with the vehicle 204, a Heating, Ventilation, and Air Conditioning (HVAC) system associated with the vehicle 204, one or more intake valves associated with the vehicle 204, an ignition system associated with the vehicle 204, one or more piston rings associated with the vehicle 204, or one or more cylinder walls associated with the vehicle 204. In an embodiment, the set of root causes may include at least one of, but is not limited to, a clogging of the catalytic converter, a leakage in the exhaust system, a leakage in the fuel injector, a failure of the HVAC system, a deposition of carbon on the one or more intake valves, a failure of the ignition system, a damage in the one or more piston rings, or a damage in the one or more cylinder walls.

By way of an example and not a limitation, if the emission value associated with the CO pollutant is high (say >0.3%), then the set of root causes (or the reasons) associated with the emission may be, but not limited to, a leakage in the exhaust system of the vehicle 204, clogging of the catalytic converter of the vehicle 204, a failure of the HVAC system of the vehicle 204, or a leakage in the fuel injector of the vehicle 204. By way of another example and not a limitation, if the emission value associated with the HC pollutant is high (say >200 ppm), then the set of root causes associated with the emission may be, but not limited to, carbon deposition on the one or more intake valves of the vehicle 204, a damage in the one or more piston rings or one or more cylinder walls of the vehicle 204, clogging of the catalytic converter of the vehicle 204, a malfunction of the ignition system of the vehicle 204.

At 320, an actions determination operation may be executed. In the actions determination operation, the system 202 may be configured to determine a set of actions to alleviate the determined set of root causes associated with the emission of the set of pollutants by the vehicle 204. In an embodiment, the set of actions may correspond to a series of specific measures or interventions that may be determined by the system 202 to address and mitigate the identified set of root causes contributing to the emission of the set of pollutants by the vehicle 204. This set of actions may be designed to resolve the underlying issues, thereby reducing the emission levels and ensuring compliance with environmental standards. Such a set of actions may be tailored to directly address the specific root causes, ensuring that the emissions from the vehicle 204 are effectively reduced and maintained within legal limits.

In an embodiment, the set of actions may include, but are not limited to, a milling operation on the set of components associated with the vehicle 204, a fabrication operation of the set of components associated with the vehicle 204, a spraying operation on the set of components associated with the vehicle 204 or a repair of the set of components associated with the vehicle 204. By way of example and not limitation, if the determined root cause corresponds to the clogging of the catalytic converter, then the determined action may correspond to cleaning of the catalytic converter of the vehicle 204 by spraying chemicals (such as decarbonization solution). As another example and not limitation, if the root cause corresponds to the failure of the HVAC system, then the determined action may correspond to the repair of the HVAC system.

At 322, it may be determined whether the set of robots 214 may be capable of executing the determined set of actions. In an embodiment, the system 202 may determine whether the set of robots 214 may be capable of executing the determined set of actions based on robot information associated with each robot of the set of robots 214. The robot information may be indicative of the capabilities of each robot of the set of robots 214, including parameters such as their operational range, tool compatibility, strength, precision, and processing speed. The system 202 may evaluate this information against the specific requirements of the actions, such as the need for particular tools, the complexity of the tasks, or the precision required, to assign the most suitable robots for executing each operation within the set of actions. In case the set of robots 214 is capable of executing the determined set of actions, then the control may be transferred to 328. Otherwise, the control may be transferred to 324.

By way of example and not limitation, if the set of actions includes the spraying operation, then the set of robots 214 may be capable of performing the spraying operation and the control may be transferred to 330. As another example, if the set of actions includes the fabrication operation or the executing operation, then the set of robots 214 may be incapable of executing the fabrication operation or the milling operation, and the control may be transferred to 324.

At 324, a recommendation generation operation may be executed. In the recommendation generation operation, the system 202 may be configured to generate a set of recommendations to alleviate the set of root causes for the emission of the set of pollutants by the vehicle 204. In an embodiment, the system 202 may be configured to generate the set of recommendations based on the determination that the set of robots 214 is incapable of executing the set of actions. Such set of recommendations may indicate the root cause and may include instructions for manual interventions, outsourcing specific tasks to external service providers, or suggesting additional equipment or tools that could enable robots or human operators to execute the required set of actions to alleviate the set of root causes for the emission of the set of pollutants by the vehicle 204.

For instance, the recommendations may suggest that certain complex repairs be handled by specialized technicians, or that specific tools or software updates be procured to enable more precise operations. In an embodiment, the system 202 may also recommend scheduling maintenance or providing guidelines to the user for manual adjustments that can be performed on the vehicle 204. Such recommendations may be generated based on a detailed analysis of the vehicle's condition, the capabilities of the robots, and the nature of the required operations, ensuring that alternative solutions are provided when automated execution is not feasible. In an embodiment, the recommendation generation process may ensure that, even if the system 202 is unable to directly address the problem, the vehicle owner or a service provider receives actionable advice to reduce emissions and maintain compliance with environmental standards.

At 326, a recommendation rendering operation may be executed. In the recommendation rendering operation, the system 202 may be configured to render the generated set of recommendations. In an embodiment, the generated set of recommendations is rendered (or presented) to the entity 216 through the infotainment unit of the vehicle 204 or the user device 210 associated with the entity 216. The system 202 may ensure that the set of recommendations is rendered in a user-friendly format, making it easy for the vehicle owner or a service operator to understand and act upon them. The set of recommendations may include actionable insights such as suggested repairs, maintenance tasks, or manual adjustments that are crucial to alleviate the root causes of the emissions from the vehicle 204. Additionally, the system 202 may display detailed explanations of the issues and the reasoning behind each recommendation, providing the user with a comprehensive understanding of the situation.

The infotainment unit may be used as a primary interface, allowing the set of recommendations to be integrated with one or more dashboard features of the vehicle 204. The entity 216 may interact with the displayed information through the touchscreen, voice commands, or other controls, allowing them to navigate through the recommendations, access detailed instructions, or even schedule service appointments directly from the interface. The infotainment unit may also provide real-time updates on the status of any automated actions being performed by the set of robots 214 or notify the entity 216 if manual intervention is required.

In an alternate embodiment, the set of recommendations may be rendered on the user device 210, such as a smartphone or tablet, via a dedicated application or notification system. The user device may allow the entity 216 to receive and review the set of recommendations remotely, enabling them to plan required actions even when they are away from the vehicle 204. The mobile application may include additional features, such as the ability to contact service providers, order parts, or track the progress of ongoing repairs. By providing flexibility in how the recommendations are delivered, the system 202 ensures that the user has convenient access to relevant information, improving the overall experience and facilitating timely corrective actions to reduce the emission of the set of pollutants from the vehicle 204.

At 328, an instructions generation operation may be executed. In the instructions generation operation, the system 202 may be configured to generate a set of instructions to control the set of robots 214 to execute the set of actions. In an embodiment, the set of instructions may be generated based on the determination that the set of robots 214 is capable of executing the set of actions. In an embodiment, the set of instructions may be designed to enable the set of robots 214 to perform the required operations (or actions) to address the set of root causes associated with the emission from the vehicle 204. As discussed above, the set of actions may include a variety of operations, such as the milling operation on specific components of the vehicle 204, the fabrication operation to produce or modify components of the vehicle 204, the spraying operation to apply coatings or treatments on specific components of the vehicle 204, and a repair operation to fix or restore components that may be contributing to increased emissions.

In an embodiment, the milling operation may involve precision machining of engine or exhaust components to correct defects or wear-related issues that may be responsible for an inefficient fuel combustion or excessive emissions. The fabrication operation may involve producing new parts or modifying existing ones to enhance vehicle performance, such as creating custom components to optimize the exhaust system or improve the function of the catalytic converter. In the spraying operation, the set of robots 214 may apply specialized coatings to reduce friction, corrosion, or heat transfer in key vehicle parts, leading to better overall efficiency and lower emissions. The repair operation involves the set of robots 214 performing repairs on damaged or malfunctioning components, such as replacing faulty sensors, sealing leaks in the exhaust system, or fixing engine components that may not function correctly. Such a set of actions is vital for restoring the vehicle to optimal working conditions and ensuring that emissions are kept within acceptable limits.

In an embodiment, the system 202 may generate the set of instructions by analyzing the set of root causes and aligning them with the capabilities of the set of robots 214. These instructions may include detailed operational parameters, such as milling depth and speed, fabrication techniques, repair procedures, and the type of spray coatings to be used. By leveraging the precision and capabilities of the set of robots 214, the system 202 ensures that the required actions are carried out effectively, addressing the root causes of the emissions problem and improving the vehicle's environmental performance. Details about the set of instructions are provided, for example, in FIG. 6.

In an embodiment, the system 202 may be configured to continuously detect pollution-dense limit using a global positioning system (GPS) associated with the vehicle 204. The system 202 may further apply the ML model 208 on the detected pollution limit. The pollution-dense limit may refer to a predefined threshold for the concentration of pollutants within a specific geographic area, beyond which the pollution is considered excessive or harmful. This limit may be determined based on environmental standards, health guidelines, or regulatory requirements, and it represents the maximum acceptable level of pollution for a given type of pollutant (e.g., particulate matter, carbon monoxide, nitrogen dioxide). If the limit exceeds the threshold, the system 202 may be configured to the set of recommendations for the engine fuel mix and burn ratio (self-tuned reference reset to the ECU) for reducing speed of the vehicle 204 which results in less rich fuel burn & lower emission.

At 330, an instructions rendering operation may be executed. In the instructions transmission operation, the system 202 may be configured to transmit the set of instructions to the set of robots 214 that are capable of executing the specified actions, such as milling, fabrication, spraying, and repairs. The transmission of instructions involves sending precise commands to the set of robots 214 over a secure communication protocol and via the WAN 104, ensuring that the commands are delivered accurately and efficiently.

The transmitted set of instructions may include all the required operational parameters, such as the specific movements, timings, and tool configurations required for each task. For example, if a milling operation is needed, the set of instructions may indicate the exact depth and speed of the milling tool. Similarly, for a repair operation, the transmitted set of instructions may indicate the steps required to replace or fix a malfunctioning component. In an embodiment, the transmission also accounts for any real-time adjustments that might be needed based on the robots' feedback or external factors, allowing for dynamic changes during execution. The system 202 may further ensure that the instructions are transmitted in a format that may be compatible with a control system of each robot of the set of robots 214, and the transmission may be verified for accuracy and completeness before the set of robots 214 may begin executing the set of actions.

At 332, a robot control operation may be executed. In the robot control operation, the system 202 may be configured to control the set of robots 214 to execute the set of actions within the vehicle 204 to alleviate the set of root causes associated with the emission of the set of pollutants. In an embodiment, the set of robots 214 may be docked within the vehicle 204. Specifically, the set of robots 214 may be docked within an engine of the vehicle 204. In an embodiment, the set of robots 214 may include at least one parent robot and at least one child robot. The at least one child robot may be associated with the at least one parent robot and may act on the commands (or instructions) received from the at least one parent robot. Details about at least one parent robot and at least one child robot are provided, for example, in FIG. 6.

In an embodiment, the system 202 may be further configured to oversee and manage the execution of the set of actions by the set of robots 214. In an embodiment, the system 202 may continuously monitor the performance of each robot of the set of robots 214, ensuring that each action is carried out according to the transmitted instructions. The robot control operation may further involve real-time feedback loops where one or more sensors associated with each robot may report their progress and any issues that may arise during the execution of milling, fabrication, spraying, or repair tasks.

The system 202 may be further configured to dynamically adjust the operations of the set of robots 214 as per the requirements, such as recalibrating tools, altering movement paths, or changing the sequence of tasks based on real-time conditions. For example, if a robot encounters an unexpected obstacle during a repair operation, the system 202 may transmit new instructions to re-route its movements or pause the operation until the issue is resolved. The controlling operation ensures that each robot executes each action with precision and efficiency, optimizing performance while minimizing errors or delays.

Throughout the robot control operation, the system 202 may provide status updates to the entity 216 via the infotainment unit or the user device 210. Such updates allow the entity 216 to track the progress of each action, receive alerts if any issues arise, and monitor the overall timeline for completing the required operations. Therefore, the system's real-time control and oversight ensure that the set of actions whether it involves milling, fabrication, spraying, or repairs are executed successfully, ultimately addressing the root causes of the emissions problem of the vehicle 204 and thereby improving its performance.

In an embodiment, the system 202 may be configured to continuously monitor the pollution levels from the external environment and adjust the fuel mix and engine firing to modified levels as the reference point is auto-adjusted such as high pollution and hence lower oxygen in the air intake or weather patterns leading to thinner air availability. The disclosed system may reset the reference by self-tuning algorithm implementation with machine learning model 208 to determine the required reference based on measured external parameters.

Figure 4:
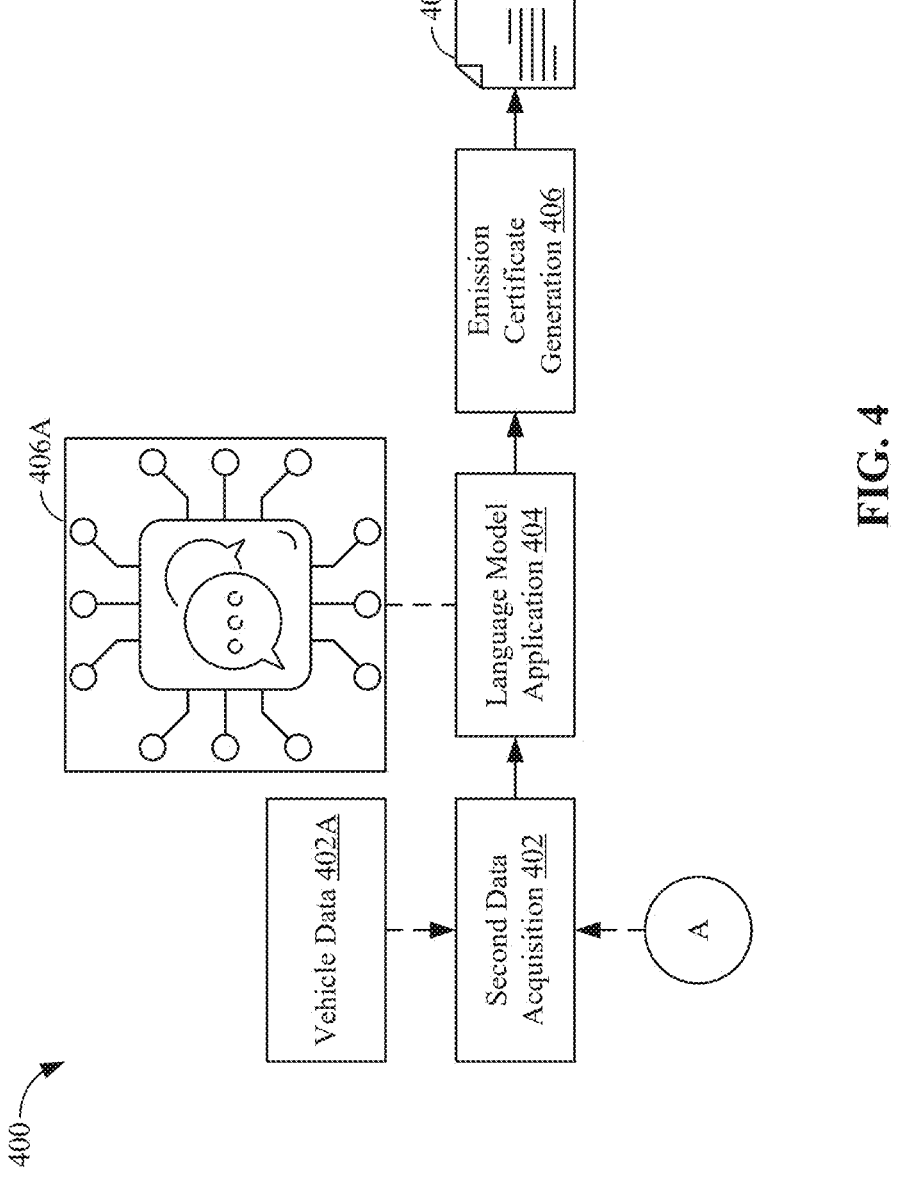
FIG. 4 is a diagram that illustrates exemplary operations for the generation of an emission certificate associated with the vehicle, in accordance with an embodiment of the disclosure.

FIG. 4 is a diagram that illustrates exemplary operations for the generation of an emission certificate associated with the vehicle, in accordance with an embodiment of the disclosure. FIG. 4 is explained in conjunction with elements from FIG. 1, FIG. 2, and FIG. 3. With reference to FIG. 4, there is shown a block diagram 400 that illustrates exemplary operations from 402 to 406, as described herein. With reference to FIG. 4, there is further shown vehicle data 402A, a language model 406A, and an emission certificate 408. The exemplary operations illustrated in the block diagram 400 may start at 402 and may be performed by any computing system, apparatus, or device, such as by the computer 102 of FIG. 1 or system 202 of FIG. 2. Although illustrated with discrete blocks, the exemplary operations associated with one or more blocks of the block diagram 400 may be divided into additional blocks, combined into fewer blocks, or eliminated, depending on the particular implementation.

At 402, a second data acquisition operation may be executed. In the second data acquisition operation, the system 202 may be configured to receive the vehicle data 402A associated with the vehicle 204. In an embodiment, the vehicle data 402A may include manufacturer data associated with the vehicle 204, model data associated with the vehicle 204, engine data associated with the vehicle 204, owner data associated with the vehicle 204, chassis data (or vehicle identification data) associated with the vehicle 204, and a registration data associated with the vehicle 204. The manufacturer data associated with the vehicle 204 may include the information about the manufacturer of the vehicle 204. As an example, the manufacturer of the vehicle may be one of, but not limited to, ABC vehicles, and XYZ cars. The model data associated with the vehicle 204 may include the information about a specific model name or a specific model number of the vehicle 204. As an example, the model number of the vehicle 204 may be one of, but not limited to, XXX001, XXX002, or XXX003.

The engine data associated with the vehicle 204 may include information associated with the engine of the vehicle 204. As discussed above, the engine of the vehicle 204 may be an internal combustion engine (ICE). The owner data associated with the vehicle 204 may include the information associated with the owner of the vehicle 204. For example, the owner data may include the name of the owner, the age of the owner, and the like. The chassis data (or vehicle identification data) associated with the vehicle 204 may be a unique number assigned to the chassis of the vehicle 204. The registration data associated with the vehicle 204 may include a registration number assigned to the vehicle 204. The registration number may correspond to a unique number that may be assigned to the vehicle 204 by the National Highway Traffic Safety Administration (NHTSA). In an embodiment, the vehicle data 402A may further include data associated with the purchase of the vehicle 204, the service details of the vehicle 204, and the insurance details of the vehicle 204.

In an embodiment, the system 202 may be configured to receive the vehicle data 402A from the set of data sources 206. Specifically, the set of data sources 206 may be connected to a set of databases associated with the National Highway Traffic Safety Administration (NHTSA). In an embodiment, the system 202 may be configured to receive the vehicle data 402A from the set of databases. In addition to the vehicle data 402A, the system 202 may be further configured to receive the determined emission value associated with the emission of the set of pollutants by the vehicle 204. Details about the emission value are provided, for example, FIG. 3.

At 404, a language model application operation is executed. In the language model application operation, the system 202 may be configured to apply the language model 406A to the vehicle data 402A and the emission value. The system 202 may apply the language model 406A based on the determination that the determined emission value is less than the threshold emission value and further based on the determination that the emission certificate associated with the vehicle 204 has expired. The system 202 may be configured to apply the language model 406A to the emission data 302A and vehicle data 402A to generate the emission certificate.

The language model 406A may be a sophisticated piece of software that leverages natural language processing (NLP) and machine learning techniques to understand, generate, and manipulate human language. For example, the language model 406A may correspond to a large language model (LLM) model that is specifically designed for tasks related to language understanding and generation on a large scale. Certain characteristics of the LLM model may include, but are not limited to, natural language understanding, text generation, semantic understanding, transfer learning, multimodal capabilities, continuous learning, and user interaction. For example, the LLM model for language processing may be implemented using GPT, Bidirectional Encoder Representations from Transformers (BERT), and the like.

Further, the LLM may be a type of ML model specifically designed to understand, generate, and manipulate human language on a large scale. LLMs may leverage machine learning techniques, particularly those based on deep learning architectures, to process and comprehend natural language. LLMs have gained prominence for their ability to perform a wide range of language-related tasks, including natural language understanding, text generation, translation, summarization, and more. Typically, LLMs may be characterized by a vast number of parameters, often ranging from tens of millions to billions. The large parameter count allows these models to capture complex language patterns and relationships during training.

For example, the LLMs may be considered to be built on Transformer architecture, however, this should not be construed as a limitation. For example, the transformer architecture effectively captures long-range dependencies and contextual information in language. Moreover, the transformer architecture may use attention mechanisms to weigh the significance of different parts of an input sequence. In addition, the LLMs may employ bidirectional processing, allowing the models to consider context from both directions when analyzing a sequence of words. This bidirectional approach enhances the model's understanding of the context in which words appear. For example, the LLMs may generate contextual representations of words, meaning that the representation of a word is influenced by its surrounding context. This enables the model to capture the meaning of words in different contexts.

Recently, the use of LLMs has increased manifold for a variety of language-related tasks, such as sentiment analysis, text classification, question answering, machine translation, summarization, and conversational agents. Due to a large number of parameters, training LLMs from scratch is a time-consuming and expensive process, and therefore, not preferable. To address this problem, pre-trained LLMs are used for generic tasks. For example, LLMs are typically pre-trained on extensive and diverse datasets containing a wide variety of text from the internet. Pre-training involves exposing the model to a broad range of language patterns, allowing it to learn general linguistic features. However, for performing domain-specific tasks, adaptation of LLMs for the particular domain needs to be performed. In one example, LLMs may leverage transfer learning where the model is pre-trained on a large corpus of data and then fine-tuned for specific tasks or domains. This approach enables the model to transfer the knowledge gained during pre-training to various downstream applications.

It may be noted that a base model in an LLM refers to a pre-trained model that has been trained on a large corpus of data for a general natural language understanding and generation task. The pre-trained model serves as a foundation for capturing broad linguistic patterns and knowledge from diverse sources. For example, in the context of pre-trained transformers, a base model is pre-trained on a massive dataset to predict the next word in a sequence, effectively learning grammar, context, and semantics from diverse language patterns.

In an example, the base model contains a large number of parameters and exhibits a high level of language understanding, making it a powerful starting point for a variety of natural language processing tasks. While the base model is pre-trained on a large corpus of general language data, fine-tuning or adapting the base model for specific tasks or domains enhances its performance and makes it more suitable for targeted applications.

Continuing further, an adapter refers to a smaller and task-specific module added to the base model to adapt the base model for a particular task or domain. The adapter includes a lightweight set of parameters that is trained on task-specific data while keeping all or the majority of the base model's parameters frozen. In particular, the adapter is used to fine-tune the base model for a specific downstream task without extensively modifying its pre-trained parameters. This approach is beneficial when computational resources or labeled task-specific data are limited.

In an embodiment, the language model 406A may be configured to generate a template associated with the emission certificate 308. The template may include a plurality of fields, which need to be populated with information from the vehicle data 402A and the emission data 302A. As an example, the template associated with the emission certificate may include at least one of the fields associated with the manufacturer data of the vehicle 204, a field associated with the model data of the vehicle 204, a field associated with the engine data of the vehicle 204, a field associated with the owner data associated with the vehicle 204, a field associated with the chassis number of the vehicle 204, or a field associated with the registration number of the vehicle 204. In another embodiment, the template may further include a field associated with the emission levels of the vehicle 204. In yet another embodiment, the template may further include a field associated with the certification period, which indicates the validity of the emission certificate 308, after which the vehicle must undergo a new emissions test, and a field associated with the certification authority.

In an embodiment, the language model 406A may be further configured to populate each field of the plurality of fields corresponding to the template associated with the emission certificate based on the vehicle data 402A and the emission values associated with the vehicle 204. As an example, the language model 406A populates the plurality of fields associated with the manufacturer data, the engine data, and the registration number based on the vehicle data 402A. As another example, the Language model 406A populates the plurality of fields associated with the emission levels of the vehicle based on a set of emission values for the set of pollutants emitted by the vehicle 204.

At 406, an emission certificate generation operation may be executed. In the emission certificate generation operation, the system 202 may be configured to generate the emission certificate based on the application of the language model 406A to the vehicle data 402A and the emission value. In an embodiment, the emission certificate 408 (or the pollution emission certificate) is a document issued by an authorized entity that certifies a vehicle's emissions are within the prescribed environmental standards set by the regulatory authorities. The emission certificate 408 serves as proof that the corresponding vehicle has undergone an emissions test and that the measured emission levels are within legally permissible limits for pollutants such as carbon oxides $(CO_x)$, nitrogen oxides $(NO_x)$, particulate matter (PM), and hydrocarbons (HC). Typically, the emission certificate 408 includes details about the vehicle 204, such as the manufacturer data associated with the vehicle 204, the model data associated with the vehicle 204, the engine type of the vehicle 204, and the registration number of the vehicle 204, along with the measured levels of various pollutants emitted by the vehicle (such as the vehicle 204).

Figure 5:
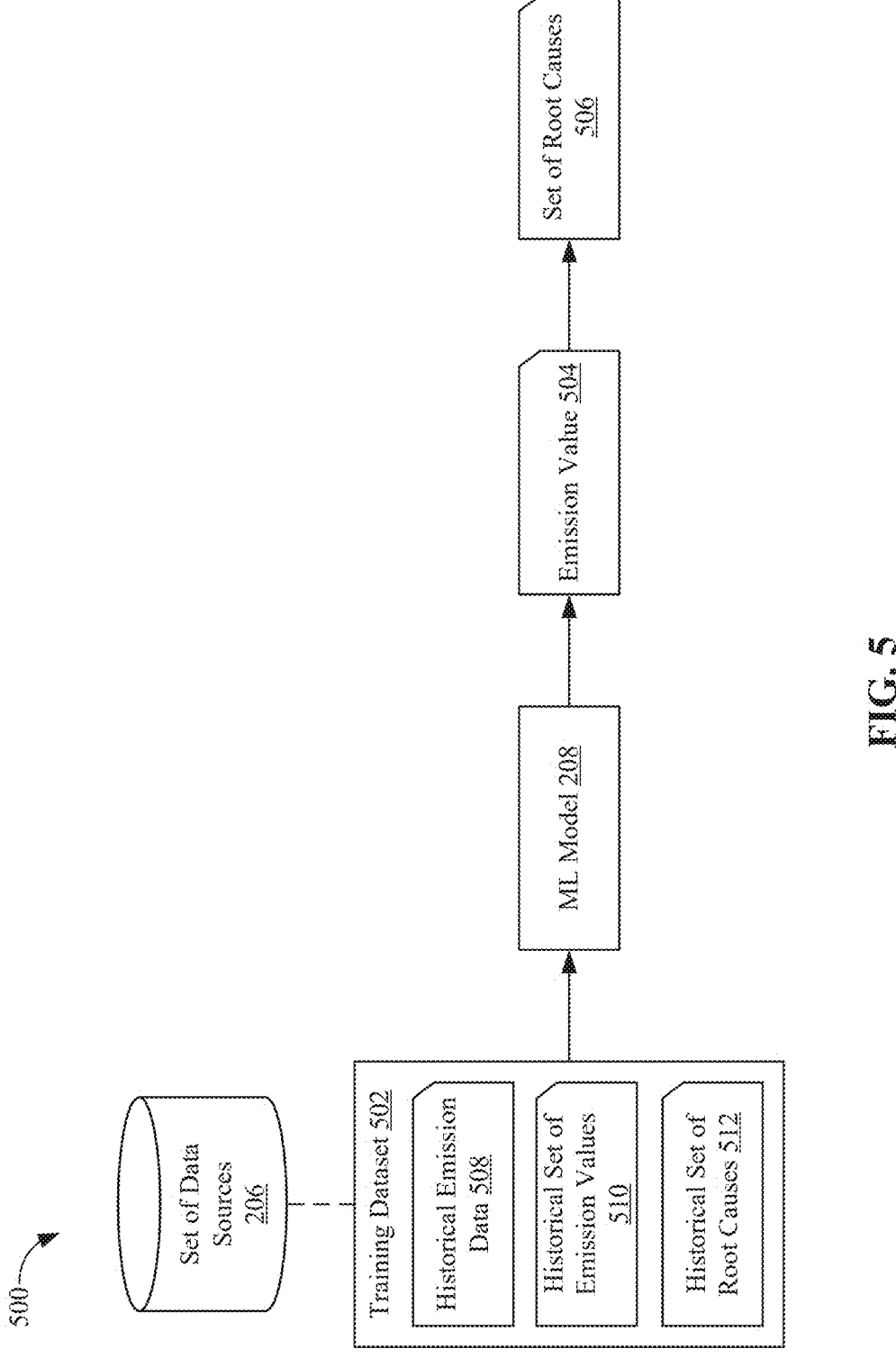
FIG. 5 is a diagram that illustrates training of an ML model for the prediction of emission value for determination and alleviation of root causes for emission of pollutants from vehicles, in accordance with an embodiment of the disclosure.

FIG. 5 is a diagram that illustrates training of an ML model for the prediction of emission value for determination and alleviation of root causes for emission of pollutants from vehicles, in accordance with an embodiment of the disclosure. With reference to FIG. 5, there is shown a diagram 500. The diagram 500 may include a training dataset 502, the emission value 504, the set of root causes 506, and the ML model 208. The training dataset 502 may include historical emission data 508, a historical set of emission values 510, and a historical set of root causes 512 associated with the emission of the set of pollutants by a set of vehicles.

In an embodiment, the training dataset 502 including the historical emission data 508 and the historical set of emission values 510 associated with the emission of the set of pollutants by the set of vehicles may be a crucial asset for developing (and improving the performance) of the ML model 208. Each emission value of the historical set of emission values 510 in the training dataset 502 may be linked to the emission of a pollutant of the set of pollutants by the corresponding vehicle of the set of vehicles, thereby providing a comprehensive view of how each emission value of the historical set of emission values was determined in the past.

released during the combustion of fuel in each engine of the corresponding vehicle of the set of vehicles. Such a set of pollutants include Carbon Monoxide (CO), a colorless and toxic gas formed from incomplete fuel combustion, and Nitrogen Oxides (NOx), which contribute to smog, acid rain, and respiratory problems. In some embodiments, a set of vehicles may also emit Particulate Matter (PM), tiny particles that can penetrate the lungs and bloodstream, causing serious health issues. Hence, the set of pollutants may include, but is not limited to, Carbon Monoxide (CO), Nitrogen Oxides (NOx), and Particulate Matter (PM). In an embodiment, the system 202 may be configured to obtain the historical emission data 508 associated with the emission of the set of pollutants by the set of vehicles. The system 202 may obtain the historical emission data 508 from the set of data sources 206.

Each emission value of the historical set of emission values 510 may be indicative of the emission of at least a first pollutant of the set of pollutants from a corresponding vehicle of the set of vehicles. Specifically, each emission value of the historical set of emission values 510 may refer to a concentration of the corresponding pollutant (say CO gas) in the exhaust gases emitted by the corresponding vehicle, expressed as a percentage of the total volume of exhaust gases or in parts per million as discussed earlier.

In an embodiment, the training dataset 502 further includes the historical set of root causes 512 associated with the emission of the set of pollutants by the corresponding vehicle of the set of vehicles. The historical set of root causes 512 may refer to the underlying factors, conditions, or issues that directly contribute to the emission of pollutants by the corresponding vehicle of the set of vehicles. In an embodiment, the historical set of root causes 512 may be associated with a malfunction of the set of components that may be associated with the corresponding vehicle of the set of vehicles. As discussed above, the set of components may include, but are not limited to, a catalytic converter associated with the corresponding vehicle, an exhaust system associated with the corresponding vehicle, a fuel injector associated with the corresponding vehicle, and the like.

In an embodiment, the system 202 may be configured to generate the training dataset 502 based on the historical emission data 508, the historical set of emission values 510, the historical weather data indicative of weather when the historical emission data 508 may have been captured, and the historical set of root causes 512. In an embodiment, a portion of the training dataset 502 is shown in Table 1:

TABLE 1

| | | | | Training Dataset | | | | |
| Weather | Catalytic Converter | Fuel Injector | CO$_2$ Emission | CO Emission | HC | NO$_2$ | CO in % | HC in (ppm) |
|---|---|---|---|---|---|---|---|---|
| Cold | Clogged | Normal | High | High | Normal | Normal | 0.5 | 200 |
| Snow | Clogged | Leak | High | High | High | Normal | 0.5 | 300 |
| Hot | Clear | Normal | Normal | Normal | Normal | Normal | 0.3 | 200 |
| Rainy | Normal | Leak | High | High | High | Normal | 0.5 | 300 |
| Extreme Cold | Clogged | Clogged | High | High | Normal | High | 0.5 | 300 |

In an embodiment, the historical emission data 508 may be associated with the emission of the set of pollutants by a set of vehicles. As discussed above, the historical emission data 508 may be associated with the emission of the set of pollutants, which may include various harmful substances In an embodiment, the system 202 may be configured to train the ML model 208 based on the training dataset 502. In an embodiment, the system 202 may be configured to train the ML model 208 to determine the emission value 504 of each pollutant of the set of pollutants based on the training dataset 502. The ML model 208 analyzes historical patterns and correlations within the training dataset 502, learning to identify a machine learning algorithm for the determination of the emission value 504 of each pollutant of the set of pollutants.

By way of an example and not a limitation, the ML model 208 may determine that a high CO emission (in the emission data) from the corresponding vehicle may correspond to the emission value of, for example, 0.5% or more. By way of another example and not a limitation, the ML model 208 may determine that a normal CO emission (in the emission data) from the corresponding vehicle may correspond to the emission value of, for example, 0.3% or less. By way of another example and not a limitation, the ML model 208 may determine that a high HC emission (in the emission data) from the corresponding vehicle may correspond to the emission value of, for example, 300 ppm or more. By way of another example and not a limitation, the ML model 208 may determine that a normal HC emission (in the emission data) from the corresponding vehicle may correspond to the emission value of, for example, 200 ppm or less.

In an embodiment, the system may further be configured to train the ML model 208 to determine the set of root causes 506 based on the training dataset 502. In an embodiment, the system 202 compares the emission values of the corresponding pollutant of the set of pollutants with the threshold emission value and then the system 202 determines the set of root causes 506 using the ML model 208.

By way of an example and not a limitation, the ML model 208 may be trained to determine that an emission value of 0.5% or greater (of CO) by the corresponding vehicle (in cold weather) may correspond to the root cause that the catalytic converter of the corresponding vehicle may be clogged. By way of another example and not a limitation, the ML model 208 may be trained to determine that an emission value of 0.5% or greater (of CO) by the corresponding vehicle (in rainy weather) may correspond to the root cause that the catalytic converter of the corresponding vehicle may be normal.

By way of another example and not a limitation, the ML model 208 may determine that an emission value of 300 ppm or greater (of HC) by the corresponding vehicle may correspond to the root cause that the fuel injector of the corresponding vehicle may be leaking. By way of another example and not a limitation, the ML model 208 may determine that an emission value of 200 ppm or lesser (of HC) by the corresponding vehicle may correspond to the root cause that the fuel injector of the corresponding vehicle may be normal.

Once the ML model 208 is trained on the training dataset 502, the system 202 may utilize the trained ML model 208 to determine the set of root causes associated with the emission of the set of pollutants by vehicles (such as the vehicle 204) in real-time. Details about the determination of the set of root causes associated with the emission of the set of pollutants by vehicles are provided, for example, in FIG. 3.

In an embodiment, the ML model 208 may be a supervised ML model 208 that may be trained with an existing vehicle emission training dataset. In an embodiment, the ML model 208 may leverage a supervised machine learning algorithm (for e.g., Linear Regression & Two-Class Classification) for predicting the emission of the set of pollutants. If the emission is beyond the threshold emission value, a neural model may be triggered to generate the set of actions for the set of robots 214 installed within the engines to fix the issue in real-time. Additionally, the system 202 may be configured to continuously monitor the emission of the set of pollutants, consume the ML model 208 inference endpoint to display the output on the infotainment unit, and further notify the regulatory authorities in case of any deviations.

Figure 6:
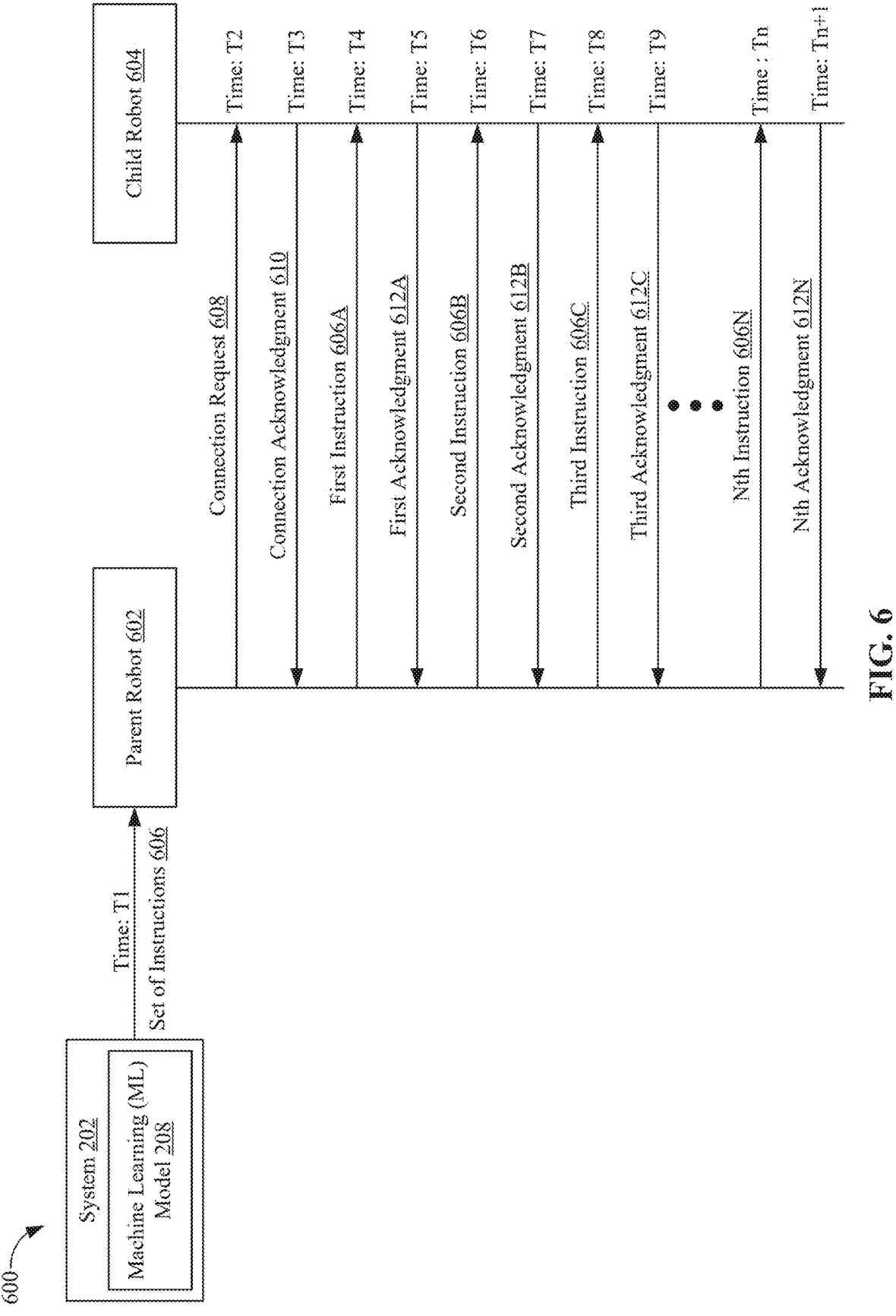
FIG. 6 is a diagram that illustrates an exemplary sequence for communication between the set of robots for the alleviation of root causes for the emission of pollutants from vehicles, in accordance with an embodiment of the disclosure.

FIG. 6 is a diagram that illustrates an exemplary sequence for communication between the set of robots for the alleviation of root causes for the emission of pollutants from vehicles, in accordance with an embodiment of the disclosure. FIG. 6 is explained in conjunction with elements from FIG. 1, FIG. 2, FIG. 3, FIG. 4, and FIG. 5. With reference to FIG. 6, there is shown an exemplary sequence 600. With reference to FIG. 6, there is further shown a parent robot 602, a child robot 604, and a set of instructions 606. The set of instructions 606 may include a first instruction 606A, a second instruction 606B, up to Nth instruction 606N.

In an embodiment, the system 202 may receive the emission data associated with an emission of the set of pollutants by the vehicle 204. The system 202 may further apply the ML model 208 to the emission data. The system 202 may further determine the set of root causes based on the application of the ML model 208 to the emission data. The set of root causes is associated with the emission of the set of pollutants by the vehicle. The system 202 may further control the set of robots 214 to execute the set of actions within the vehicle to alleviate the set of root causes associated with the emission of the set of pollutants. As a first example, the set of root causes may correspond to a clogging of the catalytic converter of the vehicle 204 and the set of actions may correspond to a spraying operation on the set of components associated with the vehicle 204.

To execute the set of actions, the system 202 may be configured to generate the set of instructions 606 to control the set of robots 214. As discussed above, the system 202 generates the set of instructions 606 based on the determination that the set of robots 214 is capable of executing the set of actions. In an embodiment, the set of robots 214 includes at least one parent robot (the parent robot 602) and at least one child robot (the child robot 604). The child robot 604 is associated with the parent robot 602. In an embodiment, the child robot 604 is docked in the engine of the vehicle 204 and the parent robot 602 may be docked at the ECU of the vehicle 204. In another embodiment, each robot of the set of robots 214 may be docked in the engine of the vehicle 204.

To execute the set of actions, the system 202 may further transmit the generated set of instructions 606 to the parent robot 602 at a time T1. By way of an example and not a limitation, the system 202 may transmit each instruction of the set of instructions 606 in the form of electromagnetic signals. Details about the set of instructions generation and the set of instructions transmission are provided, for example, in FIG. 3.

The parent robot 602 may include suitable logic, circuitry, interfaces, and/or code that may be configured to receive the set of instructions 606 from the system 202. Specifically, an electromagnetic sensor may be associated with the parent robot 602. The system 202 may transmit the set of instructions 606 (in the form of electromagnetic signals) to the electromagnetic sensor of the parent robot 602. In an embodiment, the parent robot 602 may be further configured to transmit the set of instructions 606 at a time T2 (after T1) to the child robot 604.

The child robot 604 may include suitable logic, circuitry, interfaces, and/or code that may be configured to receive the set of instructions 606 from the parent robot 602. Similar to the parent robot 602, an electromagnetic sensor may be associated with the child robot 604. The system 202 may transmit the set of instructions 606 (in the form of electromagnetic signals) to the electromagnetic sensor of the child robot 604. In an embodiment, the child robot 604 may be configured to perform the set of actions autonomously based on the set of instructions 606 received from the parent robot 602.

At time T2, the patent robot 602 may transmit a connection request 608 signal to the child robot 604. In an embodiment, the parent robot 602 transmits the connection request 608 signal to establish a connection between the parent robot 602 and the child robot 604. By way of an example and not a limitation, the connection request signal may be the electromagnetic signal. In an embodiment, the child robot 604 may receive the connection request 608 via the electromagnetic sensor associated with the child robot 604.

At time T3, the child robot 604 may transmit a connection acknowledgment 610 signal to the parent robot 602. In an embodiment, the child robot 604 may transmit the connection acknowledgment 610 signal in response to receiving the connection request 608 from the parent robot 602. By way of an example and not a limitation, the connection acknowledgment 610 may be an electromagnetic signal and may be indicative of the establishment of a connection between the parent robot 602 and the child robot 604.

At time T4, the parent robot 602 may transmit a first instruction 606A of the set of instructions 606 to the child robot 604. With reference to the first example, the parent robot 602 may transmit the first instruction 606A to instruct the child robot 604 to enter the first component of the set of components associated the vehicle 204. The first component may correspond to the catalytic converter of the vehicle 204. Specifically, the system 202 may further transmit the set of instructions 606 to the parent robot 602 for performing the set of actions to remove the clog from the catalytic converter. In this context, the parent robot 602 may further transmit the first instruction 606A to instruct the child robot 604 to enter the catalytic converter of the vehicle 204. In an embodiment, the child robot 604 may enter the catalytic converter from a nozzle entry point of the catalytic converter of the vehicle 204.

Based on the reception of the first instruction 606A, the child robot 604 may enter the catalytic converter of the vehicle 204. At time T5, the child robot 604 may transmit the first acknowledgment 612A of the set of acknowledgments to the parent robot 602. With reference to the first example, the child robot 604 may transmit the first acknowledgment 612A to the parent robot 602 after entering the catalytic converter of the vehicle 204. The first acknowledgment 612A may indicate that the parent robot 602 has entered the catalytic converter of the vehicle 204. By way of an example and not a limitation, the child robot 604 may transmit the first acknowledgment 612A in the form of electromagnetic signals.

At time T6, the parent robot 602 may transmit the second instruction 606B of the set of instructions 606 to the child robot 604 based on receiving the first acknowledgment 612A. With reference to the first example, the parent robot 602 may transmit the second instruction 606B to instruct the child robot 604 to capture one or more images of the catalytic converter of the vehicle 204. The child robot 604 may capture the one or more images of the catalytic converter and transmit the captured one or more images to at least one of the system 202 or the parent robot 602.

In an embodiment, the system 202 may be configured to determine an area of interest within the catalytic converter based on the one or more images of the catalytic converter. In an embodiment, the system 202 may be configured to generate a three-dimensional model (or 3D model of the component and determine the area of interest based on an analysis of the generated 3D model. The area of interest may correspond to an area within the catalytic converter, which may be causing an increase in the emission of the set of pollutants in comparison to the emission of the set of pollutants from the vehicle 204 in normal operating conditions. In an example embodiment, the parent robot 602 or the system 202 may determine the area of interest within the catalytic converter which may be clogged based on the one or more images of the catalytic converter.

Based on the determination of the area of interest within the catalytic converter, the system 202 may be configured to control the child robot to execute a first action of the set of actions within the area of interest to alleviate the first root cause of the set of root causes. The first robot may correspond to the child robot 604 and the first action may be associated with alleviating the first root cause. In an embodiment, the parent robot 602 may transmit a sub-instruction to control the child robot 604 to execute the first action. With reference to the first example, the parent robot 602 may transmit the sub-instruction to control the child robot 604 to spray decarbonization liquid within the area of interest of the catalytic converter to remove the clog from the catalytic converter. In an embodiment, the child robot 604 may carry multiple aerosols such as chemical sprays (such as the decarbonization liquid), degreaser containers, and the like.

At time T7, the child robot 604 may transmit the second acknowledgment to the parent robot. In an embodiment, the child robot 604 may transmit the second acknowledgment 612B in response to the second instruction 606B and further based on the execution of the first action. The child robot 604 may transmit the second acknowledgment 612B to the parent robot 602 to indicate that the first action has been executed. With reference to the first example, the child robot 604 may transmit the second acknowledgment 612B to the parent robot 602 after spraying the decarbonization liquid on the area of interest within the catalytic converter of the vehicle 204.

Based on the reception of the second acknowledgment 612B, the system 202 or the ECU of the vehicle may further determine the oxygen level and the pressure within the engine of the vehicle 204 based on the sensor data received from the set of sensors associated with the vehicle 204. The system 202 or the ECU may further compare the determined oxygen level with a predefined oxygen level threshold and the pressure with a predefined pressure threshold. In case the oxygen level is less than the predefined oxygen level threshold and the pressure is less than the predefined pressure threshold, the system 202 may generate the third instruction 606C to control the child robot 604 to exit the catalytic converter of the vehicle 204. Otherwise, it may be deemed that the catalytic converter is not unclogged completely. In such case, the system 202 may generate the third instruction 606C to control the child robot 604 to spray the decarbonization sprays again.

In case the oxygen level is less than the predefined oxygen level threshold and the pressure is less than the predefined pressure threshold, the system 202 may further generate the third instruction 606C of the set of instructions 606 and transmit the generated third instruction to the parent robot 602. The parent robot 602 may further transmit the third instruction 606C to the child robot 604.

At time T8, the parent robot 602 may transmit the second acknowledgment to the child robot. In an embodiment, the parent robot 602 may transmit the third instruction 606C to the child robot 604 to indicate that the oxygen level is below the predefined oxygen level threshold and the pressure is below the predefined pressure threshold respectively. In an embodiment, the parent robot 602 may further transmit the third instruction 606C to control the child robot to exit the first component of the vehicle. With reference to the first example, the parent robot 602 may transmit the third instruction 606C to instruct the child robot to exit the catalytic converter of the vehicle 204 and dock at its docking station. Similarly, the parent robot 602 may further transmit a fourth instruction, a fifth instruction, up to the Nth instruction 606N (if required), at time Tn, to alleviate other root causes of the set of root causes.

Based on the reception of the third instruction 606C, the child robot 604 may exit the catalytic converter of the vehicle 204. In an embodiment, the child robot 604 may exit the catalytic converter of the vehicle 204 via a tailpipe of the catalytic converter and further dock at its docking station. After docking at its docking station, the child robot 604 may transmit the third acknowledgment 612C at time T9. The child robot 604 may transmit the third acknowledgment 612C to the parent robot 602 to indicate that the child robot has exited the first component and docked at its docking station.

In an example embodiment, the child robot 604 may transmit the third acknowledgment 612C in response to the third instruction 606C based on exiting the catalytic converter of the vehicle 204 and further docking at its docking station. Similarly, the child robot 604 may further transmit a fourth acknowledgment, a fifth acknowledgment, up to the Nth acknowledgment 612N, at time Tn+1, in response to the fourth instruction, the fifth instruction, up to the Nth instruction 606N (if required).

As discussed above, each robot of the set of robots 214 may be a miniature robots installed in the engine of the vehicle and have milling/fabrication and decarbonization liquid sprays. The set of robots 214 may continuously monitor the Electronic Control Unit (ECU) in real-time and in case of abnormalities the system 202 provides the set of instructions in a message queue where the set of robots 214 takes the command and will trigger action and apply a fix in real-time. For example, if a catalytic converter is clogged, the set of robots 214 identifies the clogged area through a 3D scan to assess the problem and will spray decarbonization liquid. This miniature technology advances the way maintenance is carried out by speeding up inspections and eliminating the need to remove the engine from the vehicle 204 for repair work to take place.

Figure 7A:
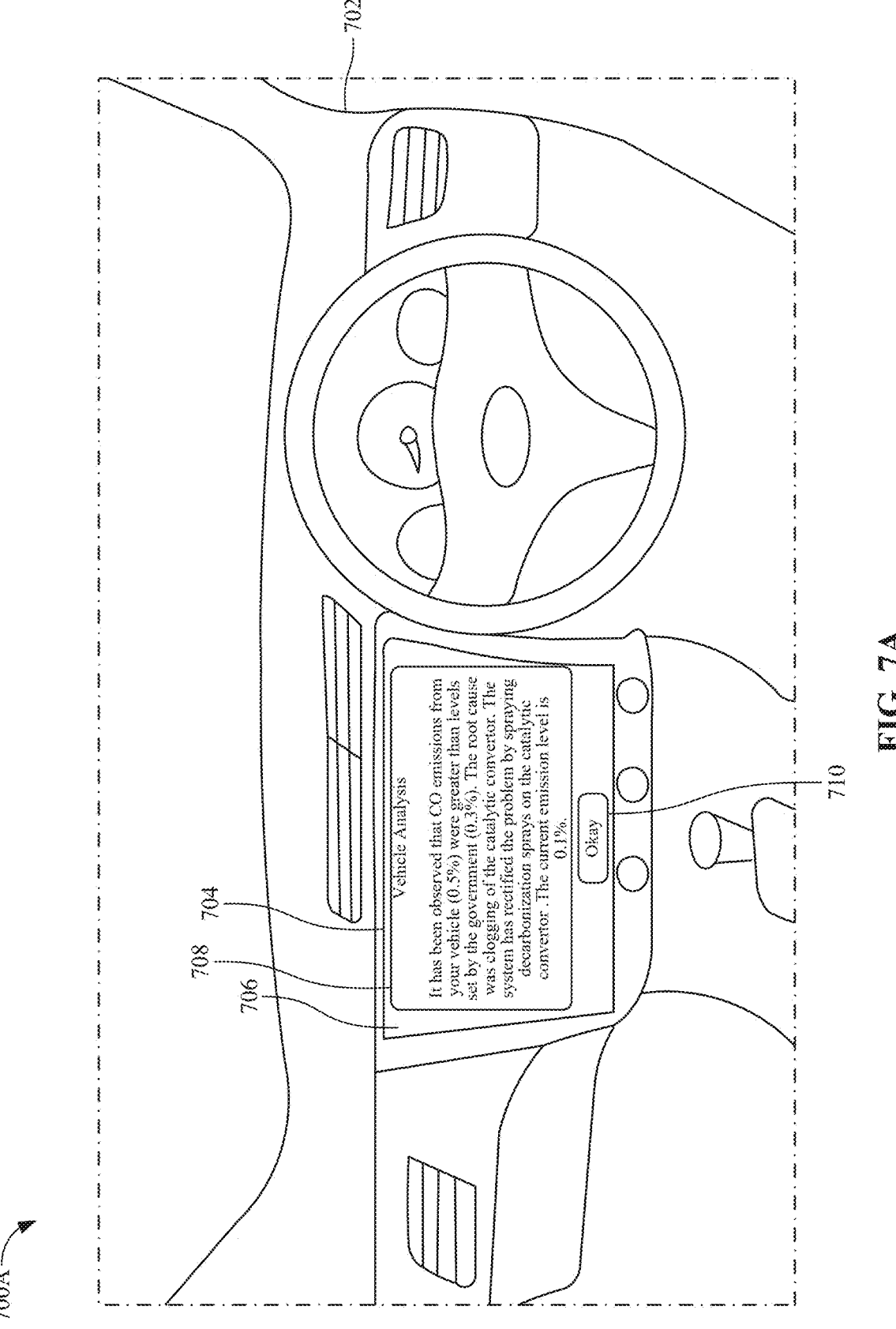
FIG. 7A is a diagram that illustrates an exemplary first scenario for rendering a message associated with the alleviation of root causes for the emission of pollutants by vehicles, in accordance with an embodiment of the disclosure.

FIG. 7A is a diagram that illustrates an exemplary first scenario for rendering a message associated with the alleviation of root causes for the emission of pollutants by vehicles, in accordance with an embodiment of the disclosure. With reference to FIG. 7A, there is shown a diagram 700A that includes a vehicle 702 and an infotainment unit 704 associated with the vehicle 702. The infotainment unit 704 includes a user interface 706, a first user interface (UI) element 708, and a second UI element 710. The vehicle 702 is an exemplary embodiment of the vehicle 204.

The infotainment unit 704 may include suitable logic, circuitry, interfaces, and/or code that may be configured to render at least one of the textual content, audio content, or video content on the user interface 706. As an example, the infotainment unit 704 may execute an operation to render a message on the user interface 706. The message may indicate the set of actions executed by the system 202 to alleviate the set of root causes associated with the emission of the set of pollutants by the vehicle 702.

As discussed above, the system 202 may be configured to determine whether the set of robots 214 is capable of executing the set of actions or not. The system 202 may then control the set of robots 214 to execute the set of actions within the set of components of the vehicle 702 based on the determination that the set of robots 214 is capable of executing the set of actions. In an embodiment, the system 202 may further be configured to render a message indicating the set of actions performed by the system 202 to alleviate the set of root causes associated with the emission of the set of pollutants from the vehicle 702. The system 202 may render the message on the user interface 706 of the infotainment unit 704 associated with the vehicle 702.

The first UI element 708 may correspond to a textbox. The textbox may include a message that may be used to indicate, to the user (say the entity 216), the set of actions performed by the system 202 to alleviate the set of root causes. The message may include, for example, "Vehicle Analysis: It has been observed that CO emissions from your vehicle (0.5%) were greater than levels set by the government (0.3%). The root cause was the clogging of the catalytic converter. The system has rectified the problem by spraying decarbonization sprays on the catalytic converter. The current emission level is 0.1%". The second UI element 710 may correspond to a button labeled "Okay". Upon selecting the second UI element 710, it may be deemed that the message in the textbox has been acknowledged by the entity 216.

Figure 7B:
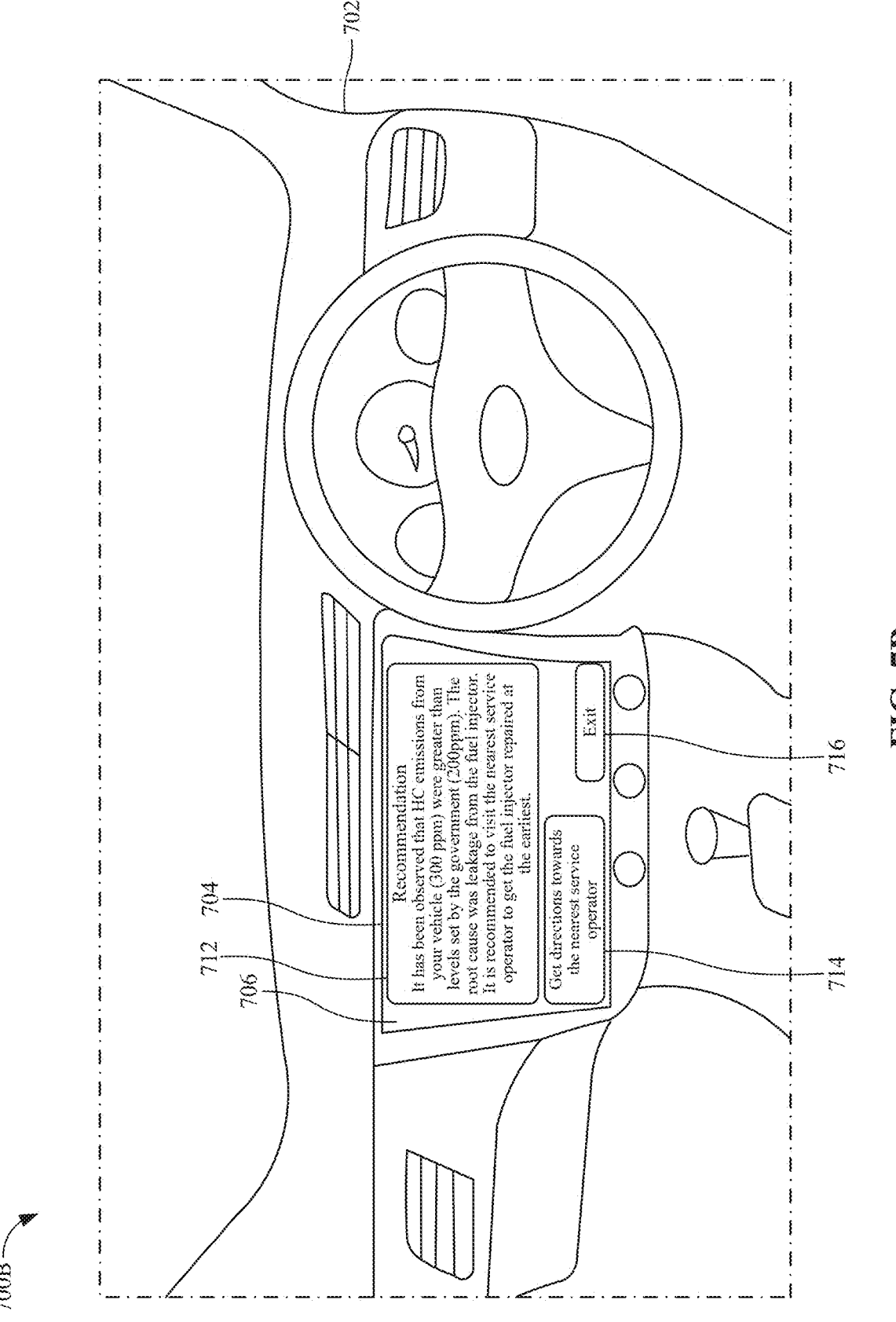
FIG. 7B is a diagram that illustrates an exemplary second scenario for rendering a recommendation associated with the alleviation of root causes for the emission of pollutants by vehicles, in accordance with an embodiment of the disclosure.

FIG. 7B is a diagram that illustrates an exemplary second scenario for rendering a recommendation associated with the alleviation of root causes for the emission of pollutants by a vehicle, in accordance with an embodiment of the disclosure. With reference to FIG. 7B, there is shown a diagram 700B that includes the vehicle 702 and the infotainment unit 704 associated with the vehicle 702. The infotainment unit 704 includes the user interface 706, a third user interface (UI) element 712, a fourth UI element 714, and a fifth UI element 716.

As discussed above, the system 202 may further be configured to generate the set of recommendations associated with the alleviation of the set of root causes for the emission of the set of pollutants by the vehicle based on the determination that the set of robots 214 is not capable of executing the set of actions. In an embodiment, the system 202 may further render the set of recommendations associated with the alleviation of the set of root causes. In an embodiment, the system 202 may render the set of recommendations on the user interface 706 of the infotainment unit 704 associated with the vehicle 702.

The third UI element 712 may correspond to a textbox. The textbox may include a recommendation for alleviating the set of root causes, for example, "Recommendation: It has been observed that HC emissions from your vehicle (300 ppm) were greater than levels set by the government (200 ppm). The root cause was leakage from the fuel injector. It is recommended to visit the nearest service operator to get the fuel injector repaired at the earliest".

The fourth UI element 714 may correspond to a button labeled as "Get directions towards the nearest repairing station". Upon selecting the fourth UI element 714, the system 202 may be configured to generate directions from the current location of the vehicle 702 to the location of a service operator of the vehicle 204. In an embodiment, the system may further be configured to render the generated directions on the user interface 706 of the infotainment unit 704 associated with the vehicle 702. The fifth UI element 716 may correspond to a button labeled "Exit". Upon selecting the fifth UI element 716, it may be deemed that the message in the textbox has been acknowledged by the entity 216.

FIG. 8 is a flowchart that illustrates an exemplary method for determination and alleviation of root causes for emission of pollutants from vehicles, in accordance with an embodiment of the disclosure. FIG. 8 is explained in conjunction with elements from FIG. 1, FIG. 2, FIG. 3, FIG. 4, FIG. 5, FIG. 6, FIG. 7A, and FIG. 7B. With reference to FIG. 8, there is shown a flowchart 800. The operations of the exemplary method may be executed by any computing system, for example, by the computer 102 of FIG. 1 or the system 202 of FIG. 2. The operations of the flowchart 800 may start at 802.

At 802, the emission data associated with the emission of the set of pollutants by the vehicle is received. The emission data is received from at least one of the vehicle or the set of data sources. In an embodiment of the disclosure, the system 202 receives the emission data associated with the emission of the set of pollutants by the vehicle. The emission data is received from at least one of the vehicle or the set of data sources 206. Details about the emission data are provided in FIG. 3.

At 804, the ML model is applied to the emission data. In an embodiment of the disclosure, the system 202 applies the ML model to the emission data. Details about the machine learning model are provided in FIG. 3, and FIG. 5.

At 806, the set of root causes is determined based on the application of the ML model to the emission data. The set of root causes is associated with the emission of the set of pollutants by the vehicle 204. In an embodiment of the disclosure, the system 202 determines the set of root causes based on the application of the ML model to the emission data. The set of root causes is associated with the emission of the set of pollutants by the vehicle 204. Details about the set of root cause determination operations are provided in FIG. 3, and FIG. 6.

At 808, the set of robots is controlled to execute the set of actions within the vehicle to alleviate the set of root causes associated with the emission of the set of pollutants. In an embodiment of the disclosure, the system 202 controls the set of robots 214 to execute the set of actions within the vehicle to alleviate the set of root causes associated with the emission of the set of pollutants. Details about the control operation are provided in FIG. 3 and FIG. 6. Control may pass to the end.

Various embodiments of the disclosure may provide a non-transitory computer-readable medium and/or storage medium having stored thereon, instructions executable by a machine and/or a computer to operate a system (e.g., the system 202) for determination and alleviation of root causes for emission of pollutants from vehicles. The instructions may cause the machine and/or computer to perform operations that include receiving emission data associated with an emission of a set of pollutants by the vehicle. The emission data is received from at least one of the vehicle or a set of data sources. The operations further include applying a machine learning (ML) model to the emission data. The operations further include determining a set of root causes based on the application of the ML model to the emission data. The operations further include controlling a set of robots to execute a set of actions within the vehicle to alleviate the set of root causes associated with the emission of the set of pollutants.

Although the disclosure is described with respect to the determination and alleviation of root causes for emission of pollutants from vehicles, the disclosure may not be limited to determination and alleviation of root causes for emission of pollutants from vehicles. The above mentioned operations may be implemented to various devices that use the ICE or the hybrid ICE such as, but not limited to, marine vehicles (like boats, fishing vessels, and jet skis), aircrafts (like helicopters), off-road vehicles (like all-terrain vehicles, and dirt bikes), agricultural and construction equipment (like tractors, harvesters, excavators, and bulldozers), power generators (like portable generators and backup power systems), small engine equipment (like lawnmowers and chainsaws), and recreational vehicles (RVs) and Campers (like motorhomes).

The descriptions of the various embodiments of the disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   receiving, by a computer, emission data associated with emission of a set of pollutants by a vehicle, wherein the emission data is received from at least one of the vehicle or a set of data sources;
   applying, by the computer, a machine learning (ML) model to the emission data;
   determining, by the computer, a set of root causes based on the application of the ML model to the emission data, the set of root causes is associated with the emission of the set of pollutants by the vehicle; and
   controlling, by the computer, a set of robots to execute a set of actions within the vehicle to alleviate the set of root causes associated with the emission of the set of pollutants.

2. The computer-implemented method of claim 1, further comprising:
   determining, by the computer, location data indicative of a location of the vehicle;
   obtaining, by the computer, weather data associated with the location of the vehicle based on the location data; and
   determining, by the computer, the set of root causes associated with the emission of the set of pollutants by the vehicle based on the application of the ML model to the weather data.

3. The computer-implemented method of claim 1, further comprising:
   determining, by the computer, the set of robots is capable of executing the set of actions to alleviate the set of root causes;
   generating, by the computer, a set of instructions to control the set of robots to execute the set of actions, wherein the set of instructions is generated based on the determination that the set of robots is capable of executing the set of actions;
   transmitting, by the computer, the set of instructions to the set of robots; and
   controlling, by the computer, the set of robots based on the transmission of the set of instructions, wherein the set of robots is controlled to execute the set of actions within the vehicle.

4. The computer-implemented method of claim 1, further comprising:

determining, by the computer, the set of robots is incapable of executing the set of actions to alleviate the set of root causes;

generating, by the computer, a set of recommendations to alleviate the set of root causes for the emission of the set of pollutants by the vehicle, wherein the set of recommendations is generated based on the determination that the set of robots is incapable of executing the set of actions; and rendering, by the computer, the set of recommendations on at least one of a user device or an infotainment unit associated with the vehicle.

5. The computer-implemented method of claim 1, wherein the set of root causes is associated with a malfunction of a set of components associated with the vehicle, and wherein the set of components comprises at least one a catalytic converter associated with the vehicle, an exhaust system associated with the vehicle, a fuel injector associated with the vehicle, a Heating, Ventilation, and Air Conditioning (HVAC) system associated with the vehicle, one or more intake valves associated with the vehicle, an ignition system associated with the vehicle, one or more piston rings associated with the vehicle, or one or more cylinder walls associated with the vehicle.

6. The computer-implemented method of claim 5, wherein the set of root causes comprises at least one of a clogging of the catalytic converter, a leakage in the exhaust system, a leakage in the fuel injector, a failure of the HVAC system, a deposition of carbon on the one or more intake valves, a failure of the ignition system, a damage in the one or more piston rings, or a damage in the one or more cylinder walls.

7. The computer-implemented method of claim 1, wherein the set of actions comprises at least one of a milling operation on a set of components associated with the vehicle, a fabrication operation of the set of components associated with the vehicle, a spraying operation on the set of components associated with the vehicle, or a repair of the set of components associated with the vehicle.

8. The computer-implemented method of claim 1, further comprising:

controlling, by the computer, the set of robots to capture one or more images of a first component of a set of components associated with the vehicle, wherein the first component is associated with a first root cause of the set of root causes;

determining, by the computer, an area of interest within the first component based on the one or more images; and controlling, by the computer, a first robot of the set of robots to execute a first action of the set of actions within the area of interest to alleviate the first root cause of the set of root causes.

9. The computer-implemented method of claim 1, further comprising:

determining, by the computer, an emission value indicative of the emission of at least a first pollutant of the set of pollutants based on the application of the ML model to the emission data; and determining, by the computer, the set of root causes for the emission of the set of pollutants by the vehicle, wherein the set of root causes is determined based on a determination that the emission value is greater than a threshold emission value.

10. The computer-implemented method of claim 1, further comprising:

determining, by the computer, an emission value indicative of the emission of at least a first pollutant of the set of pollutants, wherein the determination of the emission value is based on the application of the ML model to the emission data;

generating, by the computer, an emission certificate based on a determination that the emission value is less than a threshold emission value; and rendering, by the computer, the emission certificate on at least one of a user device, an infotainment unit associated with the vehicle, or an electronic device associated with regulatory authorities.

11. The computer-implemented method of claim 10, further comprising:

applying, by the computer, a language model to the emission data and vehicle data associated with the vehicle; and generating, by the computer, the emission certificate based on the application of the language model to the emission data and the vehicle data.

12. The computer-implemented method of claim 1, further comprising:

obtaining, by the computer, historical emission data associated with the emission of the set of pollutants by a set of vehicles;

obtaining, by the computer, a historical set of root causes for the emission of the set of pollutants by the set of vehicles;

generating, by the computer, a training dataset based on the historical emission data and historical set of root causes; and training, by the computer, the ML model based on the training dataset.

13. The computer-implemented method of claim 1, wherein the set of robots comprises at least one parent robot and at least one child robot, the at least one child robot is associated with the at least one parent robot, and wherein at least one robot of the set of robots is docked in an engine of the vehicle.

14. A system, comprising:

a processor set configured to:

receive emission data associated with emission of a set of pollutants by a vehicle, wherein the emission data is received from at least one of the vehicle or a set of data sources;

apply a machine learning (ML) model to the emission data;

determine an emission value indicative of the emission of at least a first pollutant of the set of pollutants, wherein the determination of the emission value is based on the application of the ML model to the emission data;

determine a set of root causes based on a determination that the emission value is greater than a threshold emission value, the set of root causes is associated with the emission of the set of pollutants by the vehicle; and control a set of robots to execute a set of actions within the vehicle to alleviate the set of root causes associated with the emission of the set of pollutants.

15. The system of claim 14, wherein the set of root causes is associated with a malfunction of a set of components associated with the vehicle, and wherein the set of components comprises at least one a catalytic converter associated with the vehicle, an exhaust system associated with the vehicle, a fuel injector associated with the vehicle, a Heating, Ventilation, and Air Conditioning (HVAC) system associated with the vehicle, one or more intake valves associated with the vehicle, an ignition system associated with the vehicle, one or more piston rings associated with the vehicle, or one or more cylinder walls associated with the vehicle.

16. The system of claim 15, wherein the set of root causes comprises at least one of the catalytic converter being clogged, a leakage in the exhaust system, a leakage in the fuel injector, a failure of the HVAC system, a deposition of carbon on the one or more intake valves, a failure of the ignition system, a damage in the one or more piston rings, or a damage in the one or more cylinder walls.

17. The system of claim 14, wherein the set of actions comprises at least one of a milling operation on a set of components associated with the vehicle, a fabrication operation of the set of components associated with the vehicle, a spraying operation on the set of components associated with the vehicle, or a repair of the set of components associated with the vehicle.

18. The system of claim 14, wherein the processor set is further configured to:

determine the set of robots is able to execute the set of actions to alleviate the set of root causes;

generate a set of instructions to control the set of robots to execute the set of actions, wherein the set of instructions is generated based on the determination that the set of robots is able to execute the set of actions to alleviate the set of root causes;

transmit the set of instructions to the set of robots; and control the set of robots based on the transmission of the set of instructions, wherein the set of robots is controlled to execute the set of actions within the vehicle.

19. The system of claim 14, wherein the processor set is further configured to:

determine the set of robots is unable to execute the set of actions to alleviate the set of root causes;

generate a set of recommendations to alleviate the set of root causes for the emission of the set of pollutants by the vehicle, wherein the set of recommendations is generated based on the determination that the set of robots is unable to execute the set of actions to alleviate the set of root causes; and render the set of recommendations on at least one of a user device or an infotainment unit associated with the vehicle.

20. A computer program product for an alleviation of a set of root causes associated with emission of a set of pollutants by a vehicle, comprising:

one or more computer-readable storage media; and program instructions stored on the one or more computer-readable storage media to perform operations comprising:

receiving emission data associated with the emission of the set of pollutants by the vehicle, wherein the emission data is received from at least one of the vehicle or a set of data sources;

applying a machine learning (ML) model to the emission data;

determining the set of root causes based on the application of the ML model to the emission data, the set of root causes is associated with the emission of the set of pollutants by the vehicle based on the application of the ML model to the emission data; and controlling a set of robots to execute a set of actions within the vehicle for the alleviation of the set of root causes associated with the emission of the set of pollutants.

* * * * *